US010688238B2

(12) United States Patent
Kuzelka

(10) Patent No.: US 10,688,238 B2
(45) Date of Patent: Jun. 23, 2020

(54) ANESTHESIA SYSTEM FOR CARDIOPULMONARY BYPASS MACHINE

(71) Applicant: General Electric Company, Schenectady, NY (US)

(72) Inventor: Russell James Kuzelka, McFarland, WI (US)

(73) Assignee: GENERAL ELECTRIC COMPANY, Schenectady, NY (US)

(*) Notice: Subject to any disclaimer, the term of this patent is extended or adjusted under 35 U.S.C. 154(b) by 414 days.

(21) Appl. No.: 15/721,639

(22) Filed: Sep. 29, 2017

(65) Prior Publication Data

US 2019/0099542 A1 Apr. 4, 2019

(51) Int. Cl.
| *A61M 1/36* | (2006.01) |
| *A61M 1/16* | (2006.01) |
| *A61M 39/24* | (2006.01) |
| *A61M 16/10* | (2006.01) |

(Continued)

(52) U.S. Cl.
CPC ........ *A61M 1/3666* (2013.01); *A61M 1/1698* (2013.01); *A61M 1/3632* (2014.02); *A61M 16/024* (2017.08); *A61M 16/104* (2013.01); *A61M 16/18* (2013.01); *A61M 39/24* (2013.01); *A61M 2016/103* (2013.01); *A61M 2016/1025* (2013.01); *A61M 2016/1035* (2013.01); *A61M 2202/0208* (2013.01); *A61M 2202/0241* (2013.01); *A61M 2205/3569* (2013.01); *A61M 2205/3592* (2013.01); *A61M 2205/502* (2013.01); *A61M 2205/52* (2013.01); *A61M 2209/084* (2013.01); *A61M 2230/20* (2013.01)

(58) Field of Classification Search
CPC .............. A61M 1/3666; A61M 1/1698; A61M 1/3632; A61M 16/024; A61M 16/104; A61M 16/18; A61M 39/24; A61M 2016/1025; A61M 2016/103; A61M 2016/1035; A61M 2202/0208; A61M 2202/0241; A61M 2205/3569; A61M 2205/3592; A61M 2205/502; A61M 2205/52; A61M 2209/084; A61M 2230/20
See application file for complete search history.

(56) References Cited

U.S. PATENT DOCUMENTS

| 6,934,579 B2 | 8/2005 | Mantzaridis et al. |
| 7,435,220 B2 * | 10/2008 | Ranucci ............... A61B 5/0205 |
| | | 600/483 |
| 10,086,130 B2 * | 10/2018 | Prasser ................ A61B 5/0075 |

(Continued)

FOREIGN PATENT DOCUMENTS

EP 0926984 B1 7/2007

OTHER PUBLICATIONS

Biro, P., "A Formula to Calculate Oxygen Uptake During Low Flow Anesthesia Based on FIO2 Measurement," Journal of Clinical Monitoring and Computing, vol. 14, No. 2, Feb. 1998, 4 pages.

(Continued)

*Primary Examiner* — Benjamin J Klein
(74) *Attorney, Agent, or Firm* — McCoy Russell LLP

(57) ABSTRACT

Methods and systems are provided for anesthesia systems for heart-lung machines. In one embodiment, a system comprises: a cardiopulmonary bypass machine; and an anesthesia machine operably coupled to the cardiopulmonary bypass machine, the anesthesia machine adapted to control a flow of vapor through the cardiopulmonary bypass machine.

20 Claims, 9 Drawing Sheets

(51) Int. Cl.
*A61M 16/18* (2006.01)
*A61M 16/00* (2006.01)

(56) References Cited

U.S. PATENT DOCUMENTS

| 10,463,774 B2 * | 11/2019 | Ballantyne | G05B 15/02 |
| 2008/0029091 A1 * | 2/2008 | Mullner | A61M 1/3666 |
| | | | 128/203.12 |

OTHER PUBLICATIONS

Lockwood, G. et al., "A comparison of anaesthetic tensions in arterial blood and oxygenator exhaust gas during cardiopulmonary bypass," Anaesthesia, vol. 54, No. 5, May 1999, 3 pages.

Wiesenack, C. et al., "In Vivo Uptake and Elimination of Isoflurane by Different Membrane Oxygenators during Cardiopulmonary Bypass," Anesthesiology, vol. 97, No. 1, Jul. 2002, 6 pages.

"Aisys Carestation: System Controls, Operation, Checkout, Alarms," User's Reference Manual—Software Revision 3.X, vol. 1 of 2, Available as Early as Jan. 1, 2014, 112 pages.

Barry, A. et al., "Anesthetic Management During Cardiopulmonary Bypass: A Systematic Review," Anasthesia & Analgesia, vol. 120, No. 4, Apr. 2015, 21 pages.

* cited by examiner

ANESTHESIA SYSTEM FOR CARDIOPULMONARY BYPASS MACHINE

FIELD

Embodiments of the subject matter disclosed herein relate to anesthesia systems, and more particularly, to anesthesia systems for a cardiopulmonary bypass machine.

BACKGROUND

During heart surgery, the lungs of a patient may be deflated and the heart may be temporarily stopped in order to increase a surgeon's access to the heart and reduce an amount of blood within the surgical field. Often, the heart of the patient is coupled to a cardiopulmonary bypass (CPB) machine, also referred to as a heart-lung machine (HLM), to enable extracorporeal circulation (ECC) of the blood of the patient. The blood is routed from the body of the patient through an ECC circuit of the heart-lung machine. The CPB machine provides oxygen to the blood and circulates the blood through the patient's body.

To maintain anesthesia of the patient during the surgery, volatile anesthetic agents may be administered to the blood of the patient via an anesthetic vaporizer mounted on the heart-lung machine. The anesthetic vaporizer is often positioned between a fresh gas mixer and a membrane oxygenator of the ECC circuit. Carrier gas (most typically a mixture of oxygen and fresh air) from the fresh gas mixer flows into the vaporizer and blends (e.g., mixes and converges) with the anesthetic agent vapors generated by the vaporizer. The amount of carrier gas flowing into the vaporizer may be adjusted by an operator of the vaporizer (e.g., a perfusionist) in order to adjust a ratio of carrier gas to anesthetic agents within the vaporizer. The mixed gases then flow to an inlet of the membrane oxygenator of the CPB machine in order to provide gas exchange between the blood of the patient and the mixed gases from the vaporizer. The anesthetic agents are absorbed by the blood, providing anesthesia to the patient as the blood is returned to the body.

BRIEF DESCRIPTION

In one embodiment, a system comprises: a cardiopulmonary bypass machine; and an anesthesia machine operably coupled to the cardiopulmonary bypass machine, the anesthesia machine adapted to control a flow of vapor through the cardiopulmonary bypass machine. In this way, the anesthesia machine may adjust an amount of sedation of a patient coupled with the cardiopulmonary bypass machine. In one example, the anesthesia machine may be adapted to control a flow of anesthetic vapor and/or fresh ventilation gas through an oxygenator of the cardiopulmonary bypass machine.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 1A:
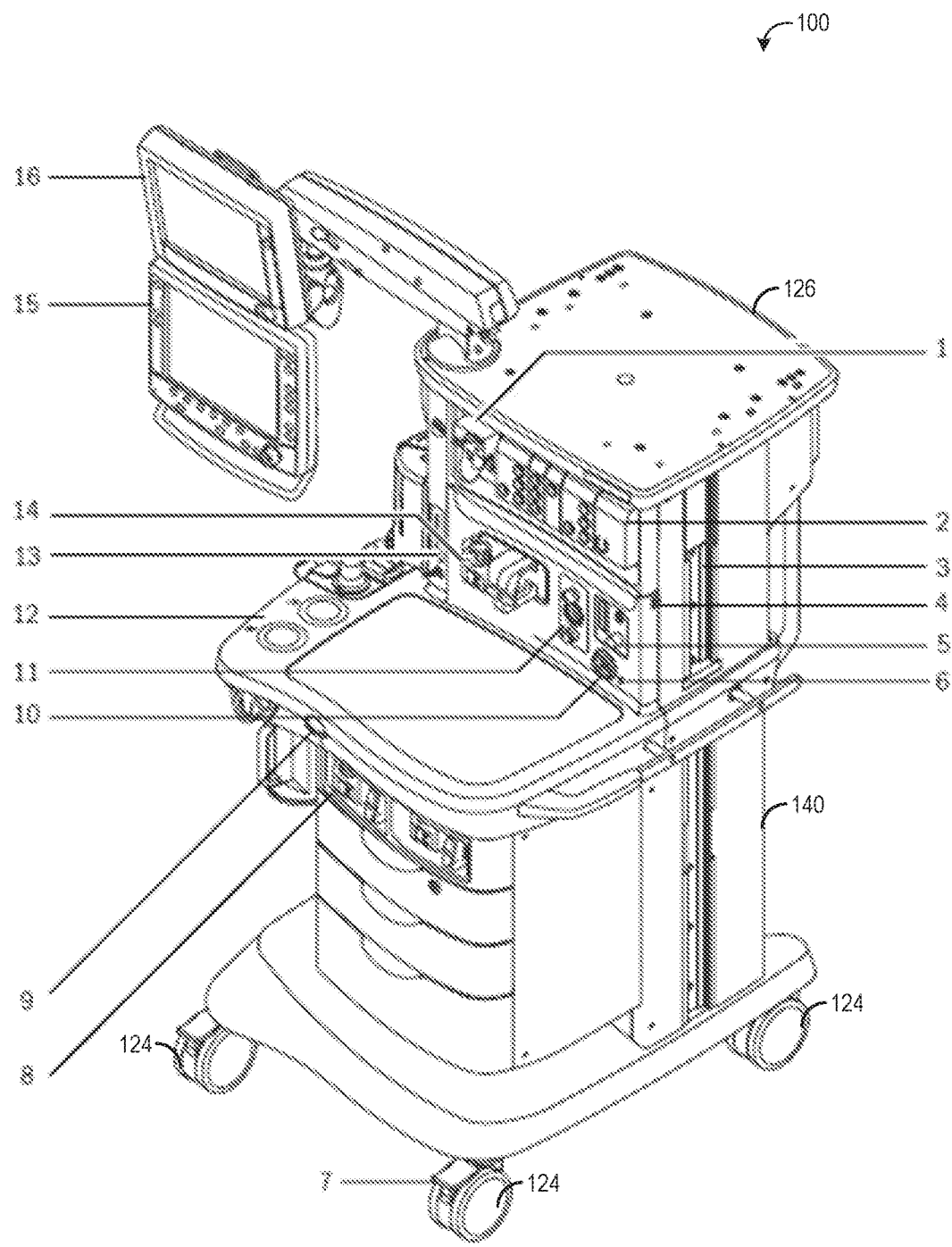
FIGS. 1A, 1B, and 1C show a first front perspective view, a second front perspective view, and back perspective view, respectively, of an anesthesia machine adapted to supply anesthetic agents to lungs of a patient, according to an embodiment of the invention.

The following description relates to various embodiments of an anesthesia system for a cardiopulmonary bypass (CPB) machine. Accurate monitoring of the level of sedation during cardiopulmonary bypass may be challenging. For example, traditional end tidal anesthesia concentration monitoring and control is not possible due to the bypass of the lungs. Further, the primary clinical signs of the depth of anesthesia, including heart rate, respiratory rate, and systemic blood pressure, are rendered useless during CPB. Cardiovascular signs which may indicate light levels of anesthesia, such as hypertension and tachycardia, are diminished due to hypotension during the start of CPB. For the duration in which the aorta is cross-clamped and the heart in asystole (pulseless), the patient's heart rate cannot be used as a sign of depth of anesthesia. Many patients undergoing coronary artery bypass graft (CABG) surgeries with CPB also receive heavy doses of medications which purposefully prevent tachycardia, so even if the patient's anesthesia is light, the heart rate is unreliable for detecting awareness. In addition to the above, the patient is also typically given a high dose of long-acting neuromuscular blocking (NMB) agents to prevent movement from surgical stimuli, which eliminates patient movement as an indicator of light anesthesia.

As explained above, during cardiopulmonary bypass the amount of anesthesia provided to a patient is typically regulated by a perfusionist by adjusting the ratio of fresh carrier gas to anesthetic vapor, generated by the vaporizer mounted on the CPB machine. In light of the challenges with monitoring the level of sedation mentioned above, it is typically not possible for the perfusionist or anesthesiologist to easily measure or predict how much anesthesia is actually being delivered to the patient, as the anesthesia machine is typically uncoupled; non-ventilating, and not measuring the end-tidal anesthetic concentration during CPB. As such, undersedation may occur with higher frequency during CPB than other medical procedures.

Furthermore, certain situations may arise in which determining the oxygenator's ventilating gas exchange (e.g., oxygen and carbon dioxide) is valuable and potentially lifesaving. For example, it may be desirable to determine whether oxygenator degradation has occurred (e.g., pneumatic circuit leaks, etc.) during conditions in which the patient is undergoing CPB, and to distinguish oxygenator gas exchange parameters associated with oxygenator degradation relative to gas exchange parameters associated with hypermetabolic states of the patient. In an example, the quality of gas exchange at the oxygenator (e.g., rate of absorption/release of gases into/from the blood of the patient within the oxygenator) may be quickly determined by use of gas concentration measurements (e.g., concentration of oxygen, carbon dioxide, and anesthetic agents) as described in this disclosure.

In one example, a first concentration of oxygen may be measured and/or estimated at an inlet of the oxygenator (e.g., with the concentration of oxygen at the inlet being based on a concentration of oxygen as measured by the fresh gas oxygen sensor of the anesthesia machine flowing from the anesthesia machine to the inlet of the oxygenator), and a second concentration of oxygen may be measured at an outlet of the oxygenator by the respiratory gas module of the anesthesia system. A difference between the first concentration and the second concentration may be determined (e.g., calculated) by the anesthesia machine, and the difference may be multiplied by a total gas flow rate from a fresh gas mixer of the anesthesia machine to the oxygenator (e.g., with the anesthesia machine physically coupled to the CPB machine to supply mixed gas to the CPB machine) in order to determine an oxygen absorption rate (which may be referred to herein as an oxygen transfer rate, oxygen uptake, or oxygen exchange rate) of the blood of the patient. In another example, the oxygen absorption rate may be determined (e.g., calculated) by the anesthesia machine according to the equation Biro–VO2=(O2 flow+[air flow*0.21])–(FiO2*fresh gas flow)/(1–FiO2), where Biro–VO2 (measured in milliliters per minute, in one example) is the rate of oxygen transport. This method typically utilizes fresh gas flow rates less than 1000 milliliters per minute (ml.min−1) with precise fresh gas flowmeter measurements, as measured by the sensors of the anesthesia machine configured to sense gas mixing and/or metering (e.g., sensors of the anesthesia machine in a flow path of the vaporizer of the anesthesia machine). The anesthesia machine may precisely measure FiO2 in order to determine the Biro-VO2. In some examples, the electronic controller of the anesthesia machine may include instructions stored in non-transitory memory for reducing aberrations in recorded FiO2 values (e.g., reducing an amount of noise of signals from the sensors described above) to reduce amplification of bias in Biro-VO2 calculations, especially at higher fresh gas flows.

In another example, a carbon dioxide ($CO_2$) absorption rate (e.g., exchange rate) of the blood of the patient at the oxygenator may be determined in a similar way. For example, the CO2 exchange rate may be determined (e.g., calculated) by the anesthesia machine according to the equation $VCO_2=Q*(FiCO_2-FeCO_2)$, where $VCO_2$ is the rate of $CO_2$ transport (e.g., $CO_2$ absorption rate), Q is the fresh gas flow rate (e.g., total mixed gas flow rate), $FiCO_2$ is the inlet gas $CO_2$ fraction (e.g., $CO_2$ concentration at the oxygenator inlet), and $FeCO_2$ is the outlet gas $CO_2$ fraction (e.g., $CO_2$ concentration at the oxygenator outlet). Typically, the inlet gas $CO_2$ fraction is zero, so the equation above reduces to $VCO_2=Q*(-FeCO_2)$, with the negative $CO_2$ exchange rate indicating that the blood of the patient releases $CO_2$ within the oxygenator.

Measurement of arterial blood carbon dioxide tension ($PaCO_2$) during cardiopulmonary bypass is important to the conduction of perfusion. Arterial temperature (e.g., blood temperature) changes during CPB may complicate attempts to monitor carbon dioxide tension in the exhaust of the membrane oxygenator, as $CO_2$ becomes more soluble with decreasing temperatures (e.g., an increased amount of CO2 may be dissolved in the blood of the patient as the temperature of the blood is reduced). During cardiopulmonary bypass, the blood of the patient may be cooled (e.g., by a heat exchanger) to temperatures (e.g., 85 degrees Fahrenheit) lower than blood temperatures during conditions in which the patient is not undergoing cardiopulmonary bypass (e.g., 98.6 degrees Fahrenheit). Lowering the blood temperature during CPB causes the patient to be in a hypothermic condition in which an amount of oxygen absorbed from the blood by the organs of the patient is reduced, thereby reducing a load (e.g., oxygen supply rate) of the oxygenator and anesthesia machine. Although the relationship of oxygenator $CO_2$ exhaust ($P_{exhaust}CO_2$) to $PaCO_2$ tension may be reasonably accurate at the lower blood temperatures, increasing the temperature of the blood from the lower temperature (e.g., 85 degrees Fahrenheit) to the higher temperature (98.6 degrees Fahrenheit) may change the relationship of the oxygenator $CO_2$ exhaust ($P_{exhaust}\ CO_2$) to $PaCO_2$ tension. Therefore, if the measured arterial temperature of the blood from the heart lung machine (e.g., from an arterial blood temperature sensor, as described below) is communicatively coupled (e.g., electronically transmitted) to the electronic controller of the anesthesia machine, a correlation between the $P_{exhaust}CO_2$ and the capnography of the anesthesia respiratory gas module may be increased for a plurality of blood temperatures. The electronic controller of the anesthesia machine may calculate $PaCO_2$ tension for a plurality of blood temperatures using a temperature correction algorithm based on linear regression, in one example.

Thus, according to embodiments disclosed herein, the CPB machine may be communicatively and/or physically coupled to the anesthesia machine during CPB. Information from the CPB machine vaporizer (mounted remotely) may be sent to the anesthesia machine, where such information may be stored and/or sent to other system computing devices (e.g., hospital servers, medical records databases for analytics, etc.). In some examples, the anesthesia machine described herein may be configured to measure the concentration of anesthetic vapor into and out of the oxygenator of the CPB machine to determine the amount of anesthesia actually absorbed into the blood of the patient, and the concentration of anesthetic vapor at the inlet of the oxygenator may be controlled in a closed-loop fashion to accurately control the amount of anesthesia provided to the patient. Further still, by allowing an anesthesiologist to monitor and control the administration of the anesthesia from the anesthesia machine, due to the communication between the anesthesia machine and CPB machine, clinical workflow may be improved.

The embodiments disclosed herein may provide several advantages. For example, the embodiments disclosed herein may facilitate and allow for automated handoff and documentation of anesthetic delivery during CPB. Further, the embodiments disclosed herein may provide for automated anesthetic delivery during CPB, thus improving clinical workflow. Additionally, the embodiments disclosed herein may provide a mechanism by which the arterial tension of volatile anesthesia in the patient's blood may be monitored and/or predicted and controlled to help mitigate potential awareness and recall during CPB.

Further still, the embodiments disclosed herein may provide additional advantages for patients undergoing cardio-pulmonary bypass surgery. For example, in embodiments in which the anesthesia machine is electronically communicatively coupled to the CPB machine and configured to flow fresh mixed ventilation gas directly to the oxygenator of the CPB machine (e.g., similar to the embodiments shown by FIGS. 3-4), the anesthesia machine may measure the composition (e.g., concentrations) of the fresh gas flow (e.g., oxygen, air, anesthetic vapor) into the membrane oxygenator. The respiratory gas module of the anesthesia machine may be configured to measure a concentration of gases output by the oxygenator (e.g., concentrations of oxygen, carbon dioxide, anesthetic vapor, etc.). The quality of gas exchange of the oxygenator (e.g., gas exchange rate with the blood of the patient) may be quickly determined via gas concentration measurements performed by the anesthesia machine, as described above with reference to the equation $VO2 = Q*(FiO2-FeO2)$ for the oxygen exchange rate and the equation $VCO2=Q*(-FeCO2)$ for the CO2 exchange rate. Determining the oxygen exchange rate and CO2 exchange rate via the measured concentrations of gases flowing to the oxygenator inlet and flowing from the oxygenator outlet may enable a clinician to more easily and/or quickly detect potential ventilation gas leaks (e.g., leaks at the oxygenator due to oxygenator degradation), elevated carbon dioxide levels (e.g., elevated CO2 concentration at the outlet of the oxygenator), and concentration of volatile anesthetic agents in the blood of the patient (e.g., to ensure sufficient levels of anesthetic agents are absorbed by the blood to maintain sedation/unconsciousness of the patient).

Figure 1B:
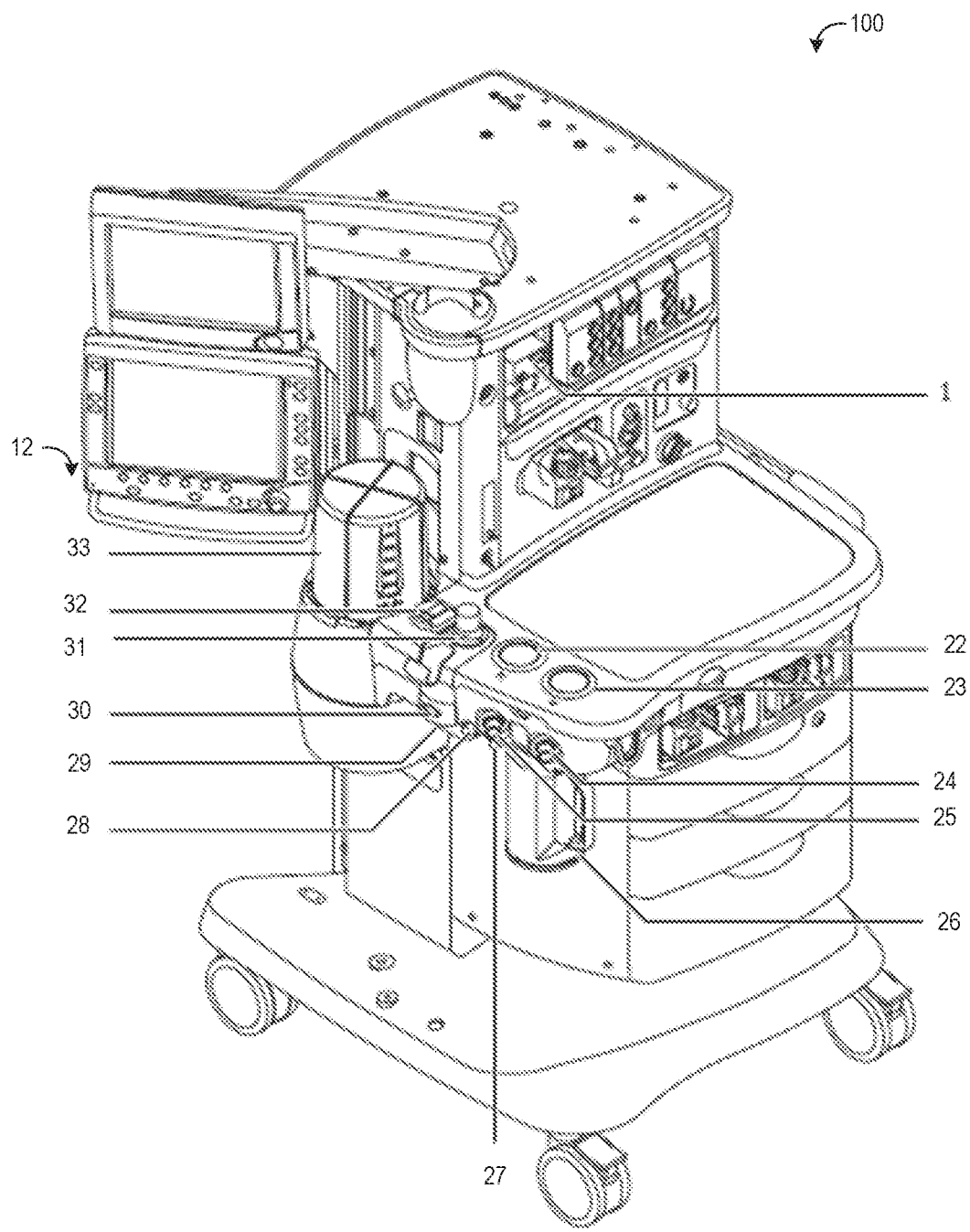
Figure 1C:
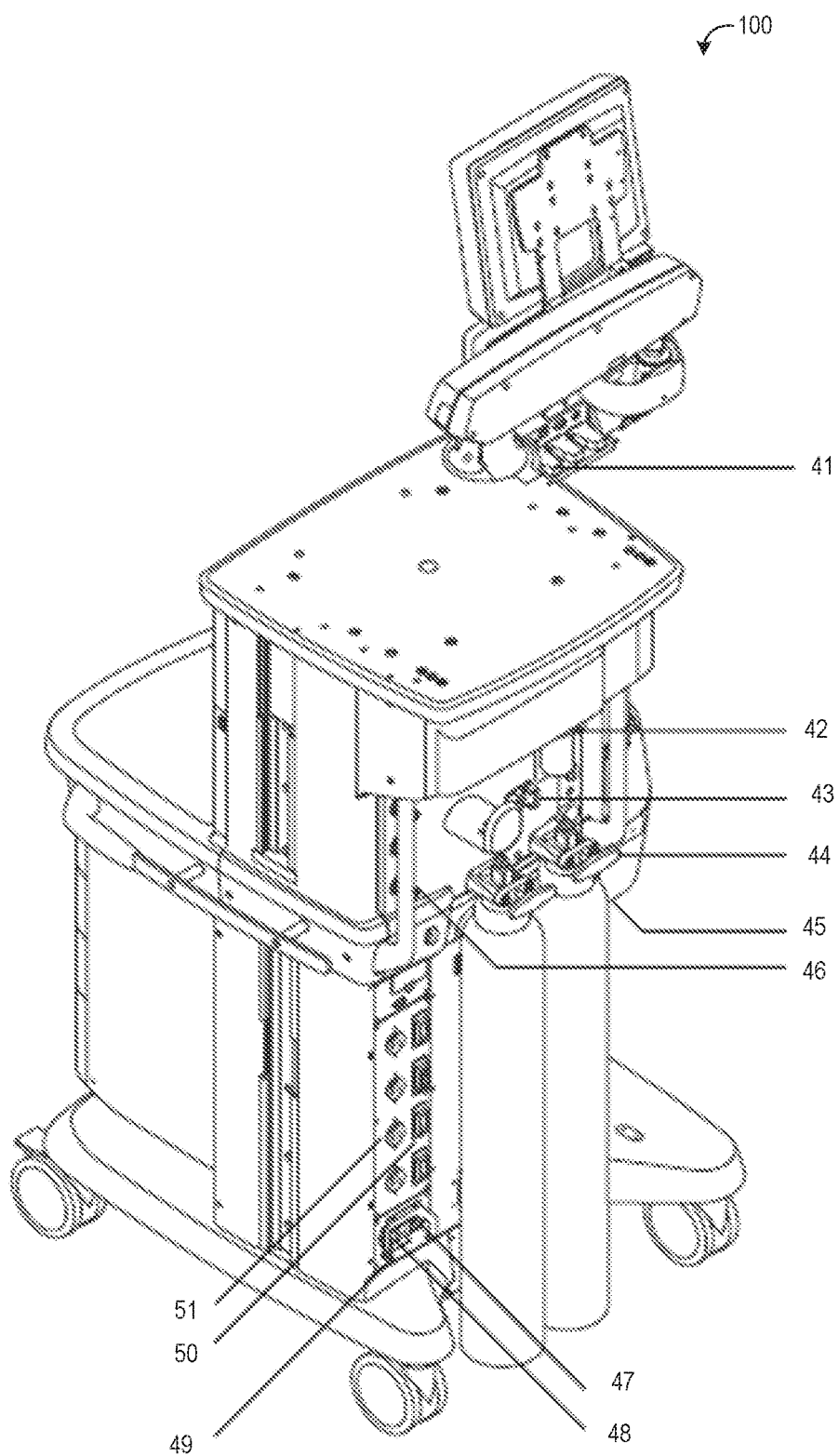

FIGS. 1A-1C show an anesthesia machine 100, from a first side perspective view (FIG. 1A), a second side perspective view (FIG. 1B), and rear perspective view (FIG. 1C). FIGS. 1A-1C will be described collectively. Anesthesia machine 100 includes a frame 126 supported by casters 124, where the movement of the casters may be controlled (e.g., stopped) by one or more locks 7. In some examples, the frame 126 may be formed of a plastic material (e.g., polypropylene). In other examples, the frame 126 may be formed from a different type of material (e.g., metal, such as steel).

Anesthesia machine 100 also includes respiratory gas module 1, one or more patient monitoring modules, such as patient monitoring module 2, side rails 3, a light switch 4, oxygen control 5, main power indicator 6, anesthetic agent storage bay 8, oxygen flush button 9, system activation switch 10 (which in one example permits gas flow when activated), integrated suction 11, ventilator 12 (explained in more detail below), auxiliary oxygen flow control 13, vaporizer 14 (explained in more detail below), anesthesia display device 15, and patient monitoring display device 16.

Vaporizer 14 may be in the form of a removable cassette such that a supply of anesthetic agent can be removed from the cassette and such that different types of anesthetic agents can be supplied to the anesthesia machine by simply removing the cassette and replacing it with a different cassette for a different anesthetic agent. The vaporizer 14 includes a housing having a drug reservoir that contains a supply of anesthetic agent to be delivered to a patient. The drug reservoir may have a discharge opening formed in a back wall of the housing that is configured to receive a discharge tube (not shown), which is part of the anesthesia machine, forming a gas-tight seal for delivery of anesthetic vapor to a patient.

Vaporizer 14 includes at least one absorbent wick within the reservoir. A passageway allows fresh gas to pass to the absorbent wick(s). The passageway allows the vaporized liquid from the absorbent wick(s) and accompanying fresh gas to flow to the back of the drug reservoir and out the discharge opening in the housing. A lower portion of the drug reservoir contains the liquid anesthetic agent and an upper portion of the reservoir contains the vaporized anesthetic agent and breathing gases. During operation, a combination of temperature and pressure affect the liquid anesthetic agent and cause it to vaporize into the breathing gases. The gases carrying the vaporized agent are then discharged through the discharge opening.

A rear of the anesthesia machine is shown in FIG. 1C. On the rear of the anesthesia machine, one or more pipeline connections 46 are present to facilitate coupling of the anesthesia machine to pipeline gas sources. Additionally, the rear of the anesthesia machine includes a cylinder yoke 44, via which one or more gas-holding cylinders may be coupled to the anesthesia machine. Thus, through the pipeline connection and/or cylinder connections, gas may be provided to the anesthesia machine, where the gas may include but is not limited to fresh gas, oxygen, and nitrous oxide. The gas that enters the anesthesia machine may mix with the vaporized anesthetic agent at the vaporizer, as described above, and be supplied to a patient via the ventilator. The rear of the anesthesia machine may also include a serial port 41, a collection bottle connection 42, cylinder wrench storage 43, anesthesia gas scavenging system 45, main power inlet 47, system circuit breaker 48, equipotential stud 49, outlet circuit breaker 50, and isolated electrical outlet 51.

The ventilator 12 may include an expiratory check valve 22, inspiratory check valve 23, inspiratory flow sensor 24, expiratory flow sensor 25, absorber canister 26, absorber canister release 27, leak test plug 28, manual bag port 29, ventilator release 30, adjustable pressure-limiting valve 31, bag/vent switch 32, and bellows assembly 33. When a patient breathing circuit is coupled to the ventilator, the breathing gases (e.g., fresh gas, oxygen, and/or nitrous oxide mixed with vaporized anesthetic agent) exit the machine from an inspiratory port (positioned at the same location as the inspiratory check valve 23) and travel to a patient. Expiratory gases from the patient re-enter the anesthesia machine via an expiratory port (positioned at the same location as the expiratory check valve 22), where the carbon dioxide may be removed from the expiratory gases via the absorber canister 26.

During operation of the vaporizer 14, an operator (e.g., an anesthesiologist) may adjust an amount of vaporized anesthetic agent that is supplied to a patient by adjusting a flow rate of gases from the gas source(s) (e.g., the gas pipelines) to the vaporizer. The flow rate of the gases from the gas source to the vaporizer may be adjusted by the operator via adjustment of one or more flow adjustment devices. For example, the flow adjustment devices may include analog and/or digital adjustment dials and/or other user input devices configured to actuate one or more flow control valves of the anesthesia machine 100. In one example, a first flow control valve may be positioned between the gas source(s) and the vaporizer 14 and may be actuatable via the flow adjustment devices to a fully opened position, a fully closed position, and a plurality of positions between the fully opened position and the fully closed position.

The anesthesia machine may additionally include one or more bypass valves configured to bypass gases from the gas source(s) around the vaporizer 14. The bypass valves may enable a first portion of gases flowing from the gas source to flow directly from the gas source to the inspiratory port, and a second portion of gases flowing from the gas source may flow through the vaporizer 14 to mix with the vaporized anesthetic agents prior to flowing to the inspiratory port. By adjusting a ratio of an amount of gases flowing to the port via the bypass valves relative to an amount of gases flowing to the port via the vaporizer 14, the operator may control a concentration of vaporized anesthetic agent in gases at the port.

Further, the adjustments described above may be facilitated at least in part based on output from the respiratory gas module 1. Respiratory gas module 1 may be configured to measure various parameters of the gases exiting the vaporizer and/or being provided to the patient. For example, respiratory gas module 1 may measure the concentrations of carbon dioxide, nitrous oxide, and anesthesia provided to the patient. Further, respiratory gas module 1 may measure respiration rate, minimum alveolar concentration, patient oxygen, and/or other parameters. The output from the respiratory gas module 1 may be displayed via a graphical user interface displayed on a display device (e.g., device 15 and/or 16) and/or used by the controller to provide closed-loop feedback control of the amount of anesthesia provided to the patient.

Ventilator 12 may optionally be coupled to a breathing circuit (not shown) including a plurality of tubes (e.g., gas passages). The breathing circuit may be coupled between an airway of a patient (e.g., via a breathing mask positioned to enclose the mouth and/or nose of the patient) and the inspiratory port. Gases (e.g., oxygen, or a mixture of oxygen and vaporized anesthetic agents from vaporizer 14) may flow from the port, through the breathing circuit, and into the airway of the patient, where the gases are absorbed by the lungs of the patient. By adjusting the concentration of vaporized anesthetic agent in the gases as described above, the operator may adjust an amount by which the patient is anesthetized.

During conditions in which the breathing circuit is coupled to the airway, anesthetic agent and/or fresh gases may flow into the airway (e.g., be inhaled by the patient) via the inspiratory check valve 23. For example, inspiratory check valve 23 may open automatically (e.g., without input or adjustment by the operator) in response to inhalation of the patient, and may close automatically in response to exhalation of the patient. Similarly, the expiratory check valve 22 may open automatically in response to exhalation of the patient, and may close automatically in response to inhalation of the patient.

In some examples, the operator may alternately and/or additionally control one or more operating parameters of the anesthesia machine 100 via an electronic controller 140 of the anesthesia machine 100. Controller 140 includes a processor operatively connected to a memory. The memory may be a non-transitory computer-readable medium and may be configured to store computer executable code (e.g., instructions) to be processed by the processor in order to execute one or more routines as described herein. The memory may also be configured to store data received by the processor. Controller 140 may be communicatively (e.g., wired or wirelessly) coupled to one or more external or remote computing devices, such as a hospital computing system, and may be configured to send and receive various information, such as electronic medical record information, procedure information, and so forth. As described below, controller 140 may also be electronically coupled to a cardiopulmonary bypass machine and may be configured to send information received from the cardiopulmonary bypass machine to the external/remote computing devices.

The controller receives signals from the various sensors of the anesthesia machine 100 and employs the various actuators of the anesthesia machine 100 to adjust operation of the anesthesia machine 100 based on the received signals and instructions stored on the memory of the controller. For example, the flow of gases to the inspiratory port may be controlled via an input device (e.g., keyboard, touchscreen, etc.) coupled to the electronic controller of the anesthesia machine 100. The controller may be electrically coupled to display device 15 and/or 16 in order to display operating parameters of the anesthesia machine 100. The controller may receive signals (e.g., electrical signals) via the input device and may adjust operating parameters of the anesthesia machine 100 in response (e.g., responsive) to the received signals. For example, the operator may input a desired flow rate of gases (e.g., oxygen) flowing from the gas source to the patient and/or vaporizer 14.

A corresponding valve position of one or more valves of the anesthesia machine (e.g., a position of one or more bypass valves, as described above) may be empirically determined and stored in a predetermined lookup table or function on the controller. For example, the controller may receive the desired flow rate of gases via the input device and may determine an amount of opening of the one or more bypass valves corresponding to the desired flow rate based on the lookup table, with an input being the desired flow rate and an output being the valve position. The controller may transmit an electrical signal to an actuator of the valve in order to adjust the valve position. In some examples, the controller may compare the desired flow rate of gases to a measured flow rate of gases as measured by a flow rate sensor of the sensors (e.g., inspiratory flow sensor 24).

In some examples, the controller may be adapted to receive wireless signals from one or more devices external to the anesthesia machine 100. For example, the controller may receive wireless signals from a cardiopulmonary bypass (CPB) machine, such as the CPB machine shown by FIG. 2 and described below. The wireless signals may include information about operating parameters of one or more components of the CPB machine (e.g., a vaporizer of the CPB machine). The controller may store the information from the wireless signals about the operating parameters of the components of the CPB machine into a non-transitory memory of the controller.

Controller 140 is shown in FIG. 1A for illustrative purposes, and it is to be understood that controller 140 may be located internally of anesthesia machine 100 and thus may not be visible externally on anesthesia machine. Controller 140 may include multiple devices/modules that may be distributed across anesthesia machine 100.

Figure 2:
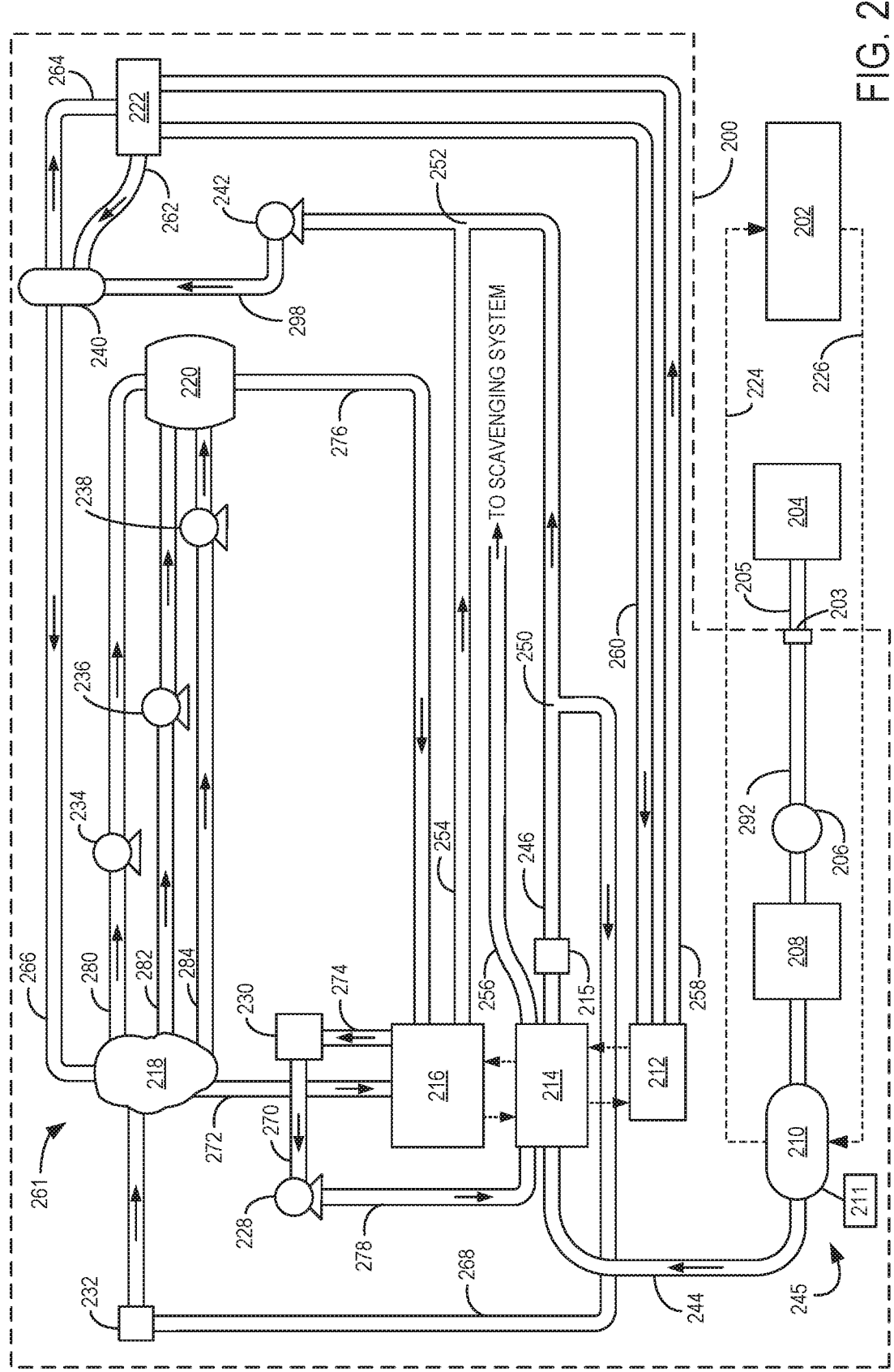
FIG. 2 schematically shows an anesthesia system including a vaporizer of a cardiopulmonary bypass (CPB) machine in wireless communication with an anesthesia machine, according to an embodiment of the invention.

FIG. 2 shows an anesthesia system 245 for a cardiopulmonary bypass (CPB) machine 200 (which may be referred to herein as a heart-lung machine). Heart-lung machine 200 includes an extracorporeal circulation (ECC) circuit 261 configured to circulate blood of a patient through the heart-lung machine 200 during conditions in which a heart 218 of the patient is coupled to the ECC circuit 261 (e.g., while heart surgery is performed on the patient).

FIGS. 2-5 each show examples of anesthesia systems having a heart-lung machine operably coupled to an anesthesia machine. Various components shown by FIGS. 2-5 may be similar to each other and may be labeled similarly. For example, components similar to the components described below with reference to FIG. 2 may be included by FIG. 3, FIG. 4, and/or FIG. 5. Components that have been introduced below with reference to FIG. 2 may not be re-introduced and may be labeled similarly in FIGS. 3, 4, and/or 5.

In the example shown by FIG. 2, the heart 218 is coupled to the ECC circuit 261 via a plurality of passages of the ECC circuit 261 (e.g., suction passage 280, suction passage 282, vent passage 284, venous passage 272, cardioplegia passage 266, and systemic flow passage 268). For example, suction passage 280 may be coupled to a first section of an aortic root of the heart 218, suction passage 282 may be coupled to the heart 218 through an incision of the heart 218, vent passage 284 may be coupled to a first section of a left ventricle of the heart 218, cardioplegia passage 266 may be coupled to a second section of the aortic root, venous passage 272 may be coupled to a second section of the left ventricle, and systemic flow passage 268 may be coupled to an aortic arch of the heart 218.

In some examples, suction passage 280 and suction passage 282 may flow blood from the heart 218 to a cardiotomy reservoir 220 via a first pump 234 and a second pump 236, respectively. Vent passage 284 may flow fluids (e.g., air) from the first section of the left ventricle of the heart 218 to the cardiotomy reservoir 220 via a third pump 238. In one example, the first pump 234, the second pump 236, and the third pump 238 may each be a roller pump. Fluids flowing from the heart 218 through the suction passage 280, suction passage 282, and vent passage 284 may mix and/or converge within the cardiotomy reservoir 220. For example, blood from the various sections of the heart 218 (e.g., the left ventricle, the aortic root, and/or the incision) may converge within an interior of the cardiotomy reservoir 220. The blood may then flow from the cardiotomy reservoir 220 to a venous reservoir 216 through a passage 276 coupled between the cardiotomy reservoir 220 and the venous reservoir 216. Additionally and/or alternately, blood may flow through the venous passage 272 from the heart 218 to the venous reservoir 216.

Figure 3:
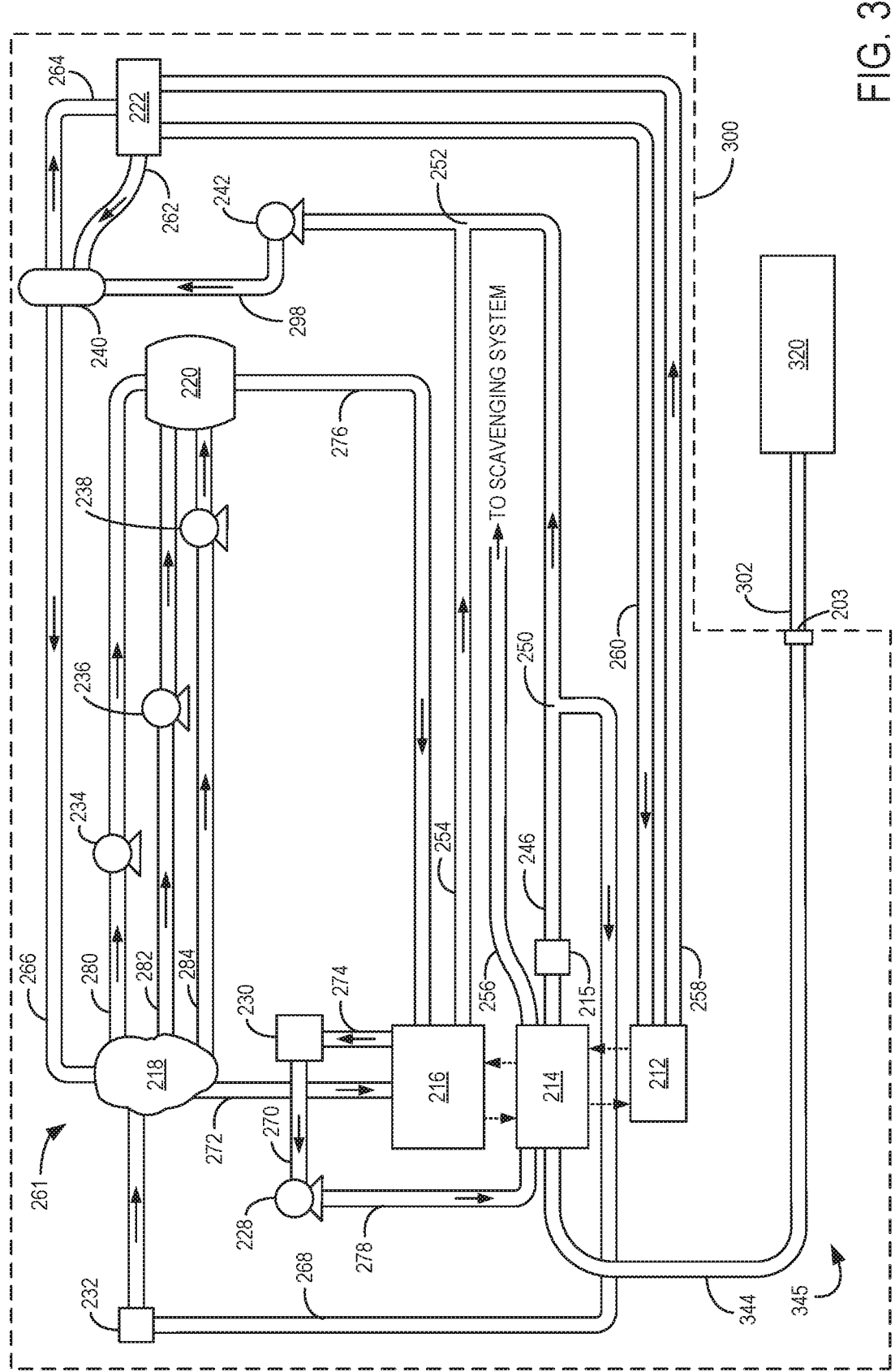
FIG. 3 schematically shows an anesthesia system including an inlet of a CPB machine directly coupled to an outlet of an anesthesia machine, according to an embodiment of the invention.
Figure 4:
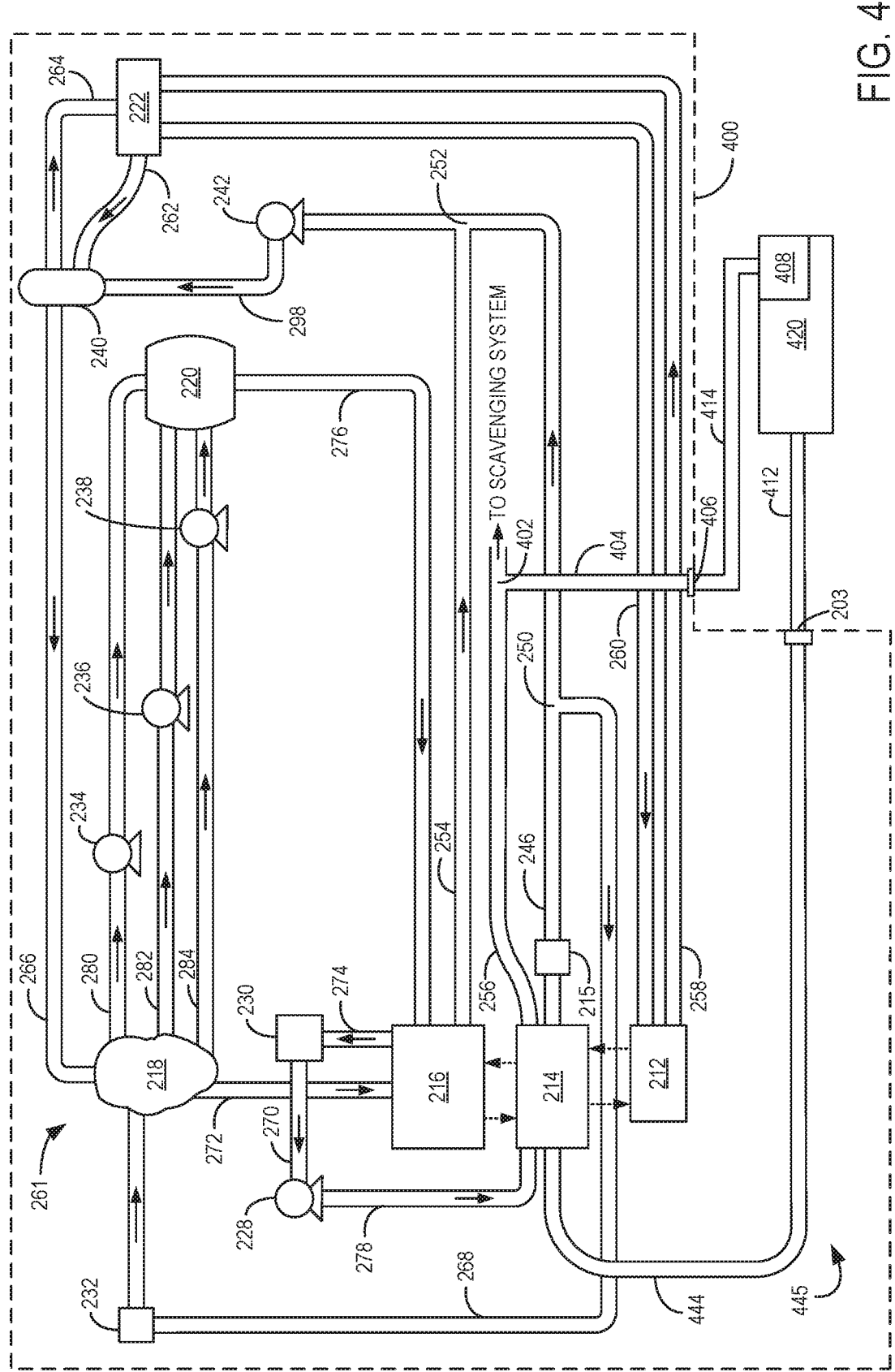
FIG. 4 schematically shows an anesthesia system including an inlet of a CPB machine directly coupled to an outlet of an anesthesia machine, and an outlet of an oxygenator of the CPB machine directly coupled to a respiratory gas module of the anesthesia machine, according to an embodiment of the invention.

Blood stored within the venous reservoir 216 may flow through an oxygenator 214 coupled to the venous reservoir 216. In the examples shown, oxygenator 214 is a membrane oxygenator configured to receive gases (e.g., oxygen, nitrous oxide, vaporized anesthetic agents, etc.) via a passage 244. Blood flows through the oxygenator 214 from the venous reservoir 216 and is oxygenated by the oxygenator 214. For example, the oxygenator 214 may include a plurality of microporous hollow fibers, and the gases received by the oxygenator 214 via passage 244 may flow through an interior of the fibers. As the gases flow through the fibers, blood from the venous reservoir 216 may flow across exterior surfaces of the fibers in order to absorb the gases within the interior of the fibers via the micropores. The oxygenator 214 may be additionally configured to remove carbon dioxide from the blood (e.g., by flowing the blood across one or more materials adapted to absorb carbon dioxide from the blood). In the example shown by FIG. 2, the gases flow through the passage 244 to the oxygenator 214 from a vaporizer 210 of the heart-lung machine 200. In alternate embodiments, gases may flow into the oxygenator 214 from a different source (e.g., from an anesthesia machine, as shown by FIGS. 3-4 and described below). Gases that are not absorbed by the blood may flow out of the oxygenator 214 via a passage 256 coupled to a gas scavenging system. The gas scavenging system may include one or more disposable materials configured to absorb the gases flowing through passage 256, and/or may vent the gases to atmosphere.

As blood flows through the oxygenator 214, a temperature of the blood may be adjusted via a heat exchanger 212 coupled to the oxygenator 214. For example, heat exchanger 212 may enable a transfer of heat from coolant (e.g., water) flowing through the heat exchanger 212 (e.g., from coolant source 222 via passage 260) to blood flowing through the oxygenator 214, and/or may enable a transfer of heat to/from blood flowing through the oxygenator 214 to coolant flowing through the heat exchanger 212. The coolant may then flow out of the heat exchanger 212 via passage 258. The oxygenator 214 may additionally include one or more sections configured to receive blood from the venous reservoir 216 via a passage 278 and to flow the blood to the oxygenator 214. In one example, the passage 278 is coupled to a systemic blood pump 228 positioned downstream of a bubble sensor 230 and the venous reservoir 216. Bubble sensor 230 may detect an amount of air bubbles within the blood flowing through the passage 278. Blood that has been oxygenated by the oxygenator 214 may flow out of the oxygenator 214 via a passage 246. Further, an arterial blood temperature sensor 215 may be positioned in passage 246. Arterial blood temperature sensor 215 may measure a temperature of the blood exiting the oxygenator 214. In some examples, the arterial blood temperature sensor 215 may be in electronic communication with an electronic controller of the heart-lung machine 200, and the electronic controller may determine a temperature of the blood flowing through the passage 246 based on signals (e.g., electrical signals) transmitted to the electronic controller by the arterial blood temperature sensor 215. The electronic controller of the heart-lung machine 200 may transmit signals (e.g., electrical and/or wireless signals) to an electronic controller of an anesthesia machine 202, and the anesthesia machine 202 may display the temperature on a graphical display device of the anesthesia machine 202 (e.g., display device 15 shown by FIG. 1A and described above) and/or calculate one or more operating parameters based on the temperature (e.g., $P_{exhaust}CO_2$, as described above).

Passage 246 is joined with systemic flow passage 268 at a first junction 250. A first amount of blood flowing through the passage 246 from the oxygenator 214 may flow through the first junction 250 toward a second junction 252, and a second amount of blood flowing through the passage 246 may flow through the first junction 250 toward a filter/bubble trap 232. The filter/bubble trap 232 may be configured to remove clots and/or bubbles from the blood flowing through the systemic flow passage 268 upstream of the heart 218. The blood may then flow from the filter/bubble trap 232 to the heart 218 via the systemic flow passage 268 as described above.

Blood flowing into the second junction 252 from the first junction 250, as well as blood flowing to the second junction 252 from the venous reservoir 216 via a passage 254, may mix and/or converge at the second junction 252 and flow to a blood cardioplegia pump 242. The blood cardioplegia pump 242 pumps blood from the second junction 252 through a passage 298 to a bubble trap/heat exchanger 240. Bubble trap/heat exchanger 240 may be configured to reduce an amount of bubbles (e.g., gaseous air) within the blood flowing from the second junction 252, and may additionally include one or more heat exchanger elements fluidly coupled with the coolant source 222 via intake passage 262 and return passage 264. For example, the heat exchanger elements of the bubble trap 240 may receive coolant flowing from the coolant source 222 via the intake passage 262, and the coolant may transfer heat to/from blood flowing through the bubble trap 240 via the passage 298. The coolant may then flow from the heat exchanger elements to the coolant source 222. Blood flowing out of the bubble trap 240 via the cardioplegia passage 266 coupled to the bubble trap 240 may flow to the heart 218 for recirculation within the ECC circuit 261.

Although not shown by FIGS. 2-5, the ECC circuit 261 of the heart-lung machine 200 may include additional components such as one or more check valves, flow valves, sensors (e.g., gas sensors, flow rate sensors, air bubble sensors, pressure sensors, etc.), filters, clamps, etc. In some examples, the various sensors of the heart-lung machine 200 may be electronically coupled (e.g., coupled electrically via one or more wires, and/or wirelessly coupled) to an electronic controller of the heart-lung machine. The electronic controller receives signals from the various sensors of the heart-lung machine 200 (e.g., sensor 215) and employs the various actuators of the heart-lung machine 200 (e.g., actuators of one or more valves, pumps, etc.) to adjust operation of the heart-lung machine 200 based on the received signals and instructions stored on a memory of the controller. For example, an operator of the heart-lung machine 200 (e.g., a perfusionist) may input desired values for one or more operating parameters of the heart-lung machine 200 (e.g., blood pumping rate, coolant temperature, etc.), and the electronic controller may adjust operation of the corresponding components of the heart-lung machine based on the operator input and the signals received from the sensors of the heart-lung machine. In one example, the electronic controller may determine a control signal to send to the blood cardioplegia pump 242 to adjust a blood pumping rate of the blood cardioplegia pump 242. The pulse width may be based on a calculation using a look-up table with the input being the desired blood pumping rate and the output being pulse-width.

In the example shown by FIG. 2, the heart-lung machine 200 includes vaporizer 210, a gas flow meter 208, a gas blender (mixer) 206, and a gas inlet 203 fluidly coupled to each other via a passage 292. The gas inlet 203 may receive gases (e.g., oxygen, air, etc.) from a gas source 204. In some examples, gas source 204 may include one or more cylinders of compressed gases or pipeline gas source. Gas blender 206 may mix and/or converge a desired ratio of gases from the gas source 204 and deliver the mixed gases to the gas flow meter 208. In one example, the desired ratio of gases (e.g., desired ratio of oxygen to air) may be input by the operator into a user input device (e.g., computer terminal) electronically coupled to the electronic controller of the heart-lung machine 200 described above. In other examples, the desired ratio of gases may be mixed by the gas blender 206 via one or more control valves of the gas blender 206. Gas flow meter 208 measures a flow rate of gases downstream of the gas blender 206 and may transmit signals (e.g., electrical signals) to the electronic controller indicating the flow rate to the controller. Alternately and/or additionally, the gas flow meter 208 may visually display the flow rate of the gases to the operator (e.g., via one or more dials, etc.).

Vaporizer 210 may be coupled to a container 211 including liquid anesthetic agents (e.g., liquid sevoflurane). The vaporizer 210 may be a plenum vaporizer, direct injection vaporizer, or other type of vaporizer configured to receive a flow of liquid anesthetic agent from the container 211 and to vaporize the liquid anesthetic agent. In some examples, the rate of vaporization of the liquid anesthetic agents may be adjusted by the electronic controller responsive to input by the operator at the user input device. In other examples, the operator may directly adjust the flow rate of liquid anesthetic agents to the vaporizer via adjustment of one or more valves coupled between the container 211 and the vaporizer 210.

In the example shown by FIG. 2, the vaporizer 210 is an electronic vaporizer configured to sense various operating parameters of the vaporizer 210 during operation of the heart-lung machine 200. For example, the vaporizer 210 may include sensors configured to detect a liquid anesthetic type from the container 211 (e.g., sevoflurane, isoflurane, etc.), liquid anesthetic level and/or liquid anesthetic flow rate from the container 211, fault codes, an amount of gases flowing into the vaporizer 210 from the gas blender 206, an amount of vaporized anesthetic agent within the vaporizer 210, a desired vapor concentration (e.g., a ratio of vaporized anesthetic agent within the vaporizer 210 relative to gases from gas blender 206 within the vaporizer 210), and/or a duration of vaporizer operation (e.g., start time and stop time of operation of the vaporizer 210).

The vaporizer 210 includes an electronic transmitter configured to transmit the sensed operating parameters (as described above) to the anesthesia machine 202 positioned external to the heart-lung machine 200. Anesthesia machine 202 is a non-limiting example of anesthesia machine 100 of FIGS. 1A-1C. In one example, the electronic transmitter may transmit wireless signals 224 (e.g., electromagnetic pulses) including information about the operating parameters of the vaporizer 210, and the wireless signals are received by the anesthesia machine 202. For example, the anesthesia machine 202 may include an electronic controller (similar to the electronic controller of the anesthesia machine 100 described above with reference to FIGS. 1A-1C), and the anesthesia machine 100 may include a wireless receiver electrically coupled to the electronic controller. The anesthesia machine 202 receives the signals 224 from the transmitter of the vaporizer 210 (e.g., via the wireless receiver) and stores the information about the operating parameters in a non-transitory memory of the anesthesia machine 202. Further, the electronic controller of the heart-lung machine 200 may send various signals to the electronic controller of the anesthesia machine 202, including but not limited to an arterial blood temperature signal from arterial blood temperature sensor 215.

The electronic controller of the anesthesia machine 202 may additionally display the operating parameters of the vaporizer 210 of the heart-lung machine 200 (e.g., as received via the wireless signals) to an operator of the anesthesia machine 202 (e.g., an anesthesiologist) via one or more graphical display devices of the anesthesia machine 202 (e.g., display device 15 shown by FIG. 1A and described above).

In some examples, the vaporizer 210 may additionally include a receiver configured to receive wireless signals from a transmitter of the anesthesia machine 202, with the transmitter of the anesthesia machine 202 being in communication with (e.g., being electrically coupled to) the electronic controller of the anesthesia machine 202. The electronic controller of the anesthesia machine 202 may transmit wireless signals to the receiver of the vaporizer 210 in order to adjust the operating parameters of the vaporizer 210. For example, the vaporizer 210 may output a mixture of vaporized anesthetic agents (e.g., liquid anesthetic agents from container 211, vaporized by the vaporizer 210) and gases (e.g., oxygen, air, etc., from the gas source 204 via gas blender 206). The ratio of vaporized anesthetic agents to gases from the gas source 204 may be referred to as an anesthetic agent concentration. An operator of the anesthesia machine 202 may input a desired anesthetic agent concentration at the user input device of the anesthesia machine 202 (e.g., keyboard, touchscreen, etc., coupled electrically to the electronic controller of the anesthesia machine), and the electronic controller of the anesthesia machine 202 may transmit a signal (e.g., electrical pulse) to the transmitter of the anesthesia machine 202. The transmitter of the anesthesia machine 202 converts the signals from the electronic controller into wireless signals 226 and transmits the wireless signals to the receiver of the vaporizer 210. The electronic controller of the vaporizer 210 adjusts the anesthetic agent concentration to the desired anesthetic agent concentration (e.g., via actuation of one or more flow rate valves of the vaporizer 210, by modifying the injection frequency of liquid anesthetic within the vaporizer, etc.) responsive (e.g., in response) to the signals received by the receiver of the vaporizer 210.

By configuring the vaporizer 210 of the heart-lung machine 200 and the anesthesia machine 202 as described above, the anesthesia machine 202 may receive signals (e.g., wireless signals) from the vaporizer 210 indicating the operating parameters of the vaporizer 210, and the operating parameters of the vaporizer 210 may be viewed by the operator of the anesthesia machine 202 via the graphical display device. The operator of the anesthesia machine 202 may additionally adjust the operating parameters of the vaporizer 210 by setting desired operating parameters at the anesthesia machine 202. The vaporizer 210 receives signals transmitted by the anesthesia machine 202 and the electronic controller of the vaporizer 210 adjusts the operating parameters of the vaporizer to the desired operating parameters in response to the received signals.

In this way, the vaporizer 210 is a self-contained, electronically controlled volatile anesthetic vaporizer with wired/wireless connectivity which enables remote set-point control of vaporizer settings. Additionally, the vaporizer 210 enables continuous vaporizer status/telemetry information communication between the vaporizer 210 and the anesthesia machine 202. This may simplify clinician workflow, increase patient monitoring quality, and facilitate automated anesthesia record-keeping and analytics during cardiopulmonary bypass procedures. Additionally, an anesthesiologist operating the anesthesia machine and a perfusionist operating the heart-lung machine may have a convenient mechanism of transitioning communicating anesthesia settings between mechanical ventilation of the patient (e.g., via a breathing circuit) and extracorporeal circulation of the blood of the patient via the heart-lung machine 200. The configuration described above enables remote adjustment of vaporizer 210 settings (e.g., operating parameters) and record keeping of volatile anesthetic agent delivery at the anesthesia machine. Examples of anesthesia record keeping may include time-stamped vaporizer fresh gas flow and concentration settings/changes, anesthetic agent concentration delivered to the heart-lung machine oxygenator, liquid anesthetic agent level, time to empty data, etc.

FIG. 3 shows an anesthesia system 345 for a heart-lung machine 300 including various components similar to the components described above with reference to the heart-lung machine 200 shown by FIG. 2. For example, heart-lung machine 300 includes venous reservoir 216, oxygenator 214, heat exchanger 212, cardiotomy reservoir 220, etc. However, in the example shown by FIG. 3, oxygenator 214 is coupled directly to gas inlet 203 via passage 344. Specifically, the heart-lung machine 300 shown by FIG. 3 may include components (not shown) that are similar to the vaporizer 210, gas flow meter 208, and gas blender 206 shown by FIG. 2, but the components are not fluidly coupled by the passage 344 to the gas inlet 203.

The gas inlet 203 is coupled to a passage 302 positioned external to the heart-lung machine 300. The passage 302 fluidly couples the gas inlet 203 to an anesthesia machine 320, similar to the anesthesia machine 100 shown by FIGS. 1A-1C and the anesthesia machine 202 shown by FIG. 2, as described above. Anesthesia machine 320 is configured to flow gases through the gas inlet 203 to the oxygenator 214 of the heart-lung machine 300.

In one example, the anesthesia machine 320 may flow fresh gases (e.g., oxygen, air, etc.) from a gas source of the anesthesia machine 320 (e.g., the gas sources described above with reference to FIGS. 1A-1C) to the oxygenator 214 via the passages 302 and 344 coupled to the gas inlet 203. Anesthesia machine 320 additionally includes a vaporizer (e.g., similar to the vaporizer 14 described above with reference to FIGS. 1A-1C) for vaporizing liquid anesthetic agents and blending the vaporized anesthetic agents with the fresh gases prior to delivery to the oxygenator 214.

By coupling the anesthesia machine 320 directly to the gas inlet 203 of the heart-lung machine 300, connectivity between a control panel of the heart-lung machine and the anesthesia machine would enable an operator (e.g., a perfusionist) to remotely adjust mixed gas and vaporizer settings of the anesthesia system. Anesthetic delivery into the ECC circuit thus may occur directly via the anesthesia workstation, off-loading the perfusionist to concentrate on other heart-lung machine operating parameters.

FIG. 4 shows an anesthesia system 445 for a heart-lung machine 400 including various components similar to the components described above with reference to the heart-lung machine 200 shown by FIG. 2 and the heart-lung machine 300 shown by FIG. 3. For example, heart-lung machine 400 includes venous reservoir 216, oxygenator 214, heat exchanger 212, cardiotomy reservoir 220, etc. However, in the example shown by FIG. 4, the passage 256 coupling the oxygenator 214 to the gas scavenging system is additionally joined with passage 404 at a junction 402. The passage 404 is coupled to a second gas outlet 406 of the heart-lung machine 400, and the second gas outlet 406 is fluidly coupled to a respiratory gas module 408 of anesthesia machine 420 (e.g., similar to the respiratory gas module 1 of the anesthesia machine 100 shown by FIGS. 1A-1C and described above).

A first portion of gases (e.g., oxygen and/or air mixed with vaporized anesthetic agents) may flow from the oxygenator 214 to the scavenging system via the passage 256, and a second portion of the gases may flow from the oxygenator 214 to the second gas outlet 406 via the passage 404 joined to junction 402. Said another way, the first portion of gases flows from the junction 402 to the scavenging system, and the second portion of gases flows from the junction 402 to the second gas outlet 406.

The respiratory gas module 408 includes one or more sensors configured to sense an amount of vaporized anesthetic agent within the second portion of the gases. An electronic controller of the anesthesia machine (e.g., similar to the electronic controller described above with reference to the anesthesia machine 100 shown by FIGS. 1A-1C) may receive signals (e.g., electrical signals) from the respiratory gas module 408 in order to determine the amount of vaporized anesthetic agent within the second portion of the gases. In one example, the electronic controller may determine the amount of vaporized anesthetic agent within the second portion of gases based on an electrical pulse width and/or amplitude of signals from the respiratory gas module 408 to the electronic controller, with increased pulse width and/or amplitude corresponding to an increased amount of vaporized anesthetic agent.

Similar to the example of the anesthesia machine shown by FIG. 3 and described above, anesthesia machine 420 is configured to flow fresh gases (e.g., oxygen, air, etc.) from a gas source of the anesthesia machine 420 (e.g., the gas sources described above with reference to FIGS. 1A-1C) to the oxygenator 214 via passages 444 and 412 coupled to the gas inlet 203. Anesthesia machine 420 additionally includes a vaporizer (e.g., similar to the vaporizer 14 described above with reference to FIGS. 1A-1C) for vaporizing liquid anesthetic agents and blending the vaporized anesthetic agents with the fresh gases prior to delivery to the oxygenator 214.

The amount of vaporized anesthetic agents flowing from the anesthesia machine 420 to the oxygenator 214 may be determined by the electronic controller of the anesthesia machine 420 via one or more sensors of the anesthesia machine 420 (e.g., similar to the sensors described above with reference to FIGS. 1A-1C). The electronic controller may compare the amount of vaporized anesthetic agents flowing from the anesthesia machine 420 (e.g., via passage 412) to the amount of vaporized anesthetic agents flowing to the respiratory gas module 408 (e.g., via the passage 414) in order to determine an amount of vaporized anesthetic agent absorbed by the blood of the patient (e.g., the blood flowing through ECC circuit 261).

For example, the anesthesia machine 420 may flow vaporized anesthetic agents and fresh gases (e.g., oxygen, air, etc.) to the oxygenator 214, with a ratio of vaporized anesthetic agents to fresh gases being at a first ratio (e.g., a first concentration of vaporized anesthetic agents to fresh gases). The oxygenator 214 may flow vaporized anesthetic agents and fresh gases to the respiratory gas module 408, with a ratio of the vaporized anesthetic agents to fresh gases being at a second ratio (e.g., a second concentration of vaporized anesthetic agents to fresh gases). The electronic controller may compare the first ratio to the second ratio in order to determine an absorption rate of the vaporized anesthetic agent into the blood of the patient (e.g., a mass of anesthetic agent absorbed by the blood per unit time, as one non-limiting example). In another example, the difference in ratios between the input and output anesthetic vapor concentrations, as described previously, may be combined with information of the systemic blood pump speed 228 (e.g., flow rate) from the heart-lung machine 400 to calculate uptake of the anesthetic agent in the patient's blood via the membrane oxygenator 214.

In some examples, an operator of the anesthesia machine 420 may input a desired anesthetic agent absorption rate into a user input device (e.g., keyboard, touchscreen, etc.) of the anesthesia machine 420, and the electronic controller of the anesthesia machine 420 may adjust operating parameters of the anesthesia machine 420 (e.g., flow rate of gases from the anesthesia machine 420, flow rate of liquid anesthetic agent to the vaporizer of the anesthesia machine 420, etc.) in order to provide the desired anesthetic agent absorption rate. In one example, the operator may input an increased desired anesthetic agent absorption rate via the user input device (e.g., in order to increase a sedation of the patient), and in response, the electronic controller may increase a flow rate of vaporized anesthetic agents to the oxygenator 214 via the anesthesia machine 420.

By configuring the anesthesia system 445 as described above, the anesthesia system may be utilized to provide closed loop control of volatile anesthetic agent delivered into the patient's blood stream via the oxygenator of the heart-lung machine by monitoring the anesthetic agent concentration into and out of the oxygenator. The anesthetic agent concentration input into the oxygenator is measured by the anesthesia machine, and the output exhaust anesthetic agent concentration of the oxygenator is monitored by the respiratory gas module of the anesthesia system. The difference between input and exhaust vapor concentration, may be correlated/modeled to predict the tension of the anesthetic agent in the patient's arterial blood, thereby increasing an accuracy with which anesthetic agent may be dosed to the patient. This prediction may further be improved by incorporating pump speed information transmitted from the heart lung machine 400 to the anesthesia machine 420.

The anesthesia machine may also be used to determine potential pneumatic leak points of the ventilating gas to the oxygenator 214 by executing a pneumatic leak test prior to the start of a procedure. For example, prior to flowing a patient's blood through the oxygenator, the concentration of oxygen, carbon dioxide, and/or vaporized anesthetic agent in the fresh gas mixture exiting the anesthesia machine and traveling to the oxygenator (e.g., via passages 444 and 412) may be measured by the anesthesia machine. Likewise, the concentration of oxygen, carbon dioxide, and/or vaporized anesthetic agent in the exhausted gas mixture exiting the oxygenator (e.g., and traveling to the anesthesia machine via passages 404 and 414) as well as the temperature of the blood exiting the oxygenator may be measured by the respiratory gas module of the anesthesia machine and arterial blood temperature sensor 215. If the difference between the oxygen concentration, for example, upstream and downstream of the oxygenator is greater than a threshold, it may be determined that a pneumatic leak exists in the system.

In still further examples, a leak or other degradation of the system may be differentiated from a hypermetabolic state of the patient (e.g., where the patient is uptaking a relatively high amount of oxygen and/or vaporized agent). For example, a relatively low oxygen concentration in the exhausted gas exiting the oxygenator may be indicative of a high uptake of oxygen by the patient, or it may be indicative of a leak in the heart-lung machine, for example. However, if the concentration of the oxygen upstream of the oxygenator is also measured (e.g., by the anesthesia machine), and the flow rate of the fresh gas mixture is determined (e.g., total mixed gas flow rate from the anesthesia machine to the oxygenator), the low oxygen concentration at the outlet of the oxygenator may be attributed to high oxygen uptake by the blood of the patient if the concentration of oxygen flowing to the inlet of the oxygenator is relatively high/expected (and hence the difference between the oxygen concentration at the inlet and outlet of the oxygenator is high).

On the other hand, during some conditions, the low oxygen concentration at the outlet of the oxygenator may be attributed to a leak or other degradation of the oxygenator, CPB machine, and/or anesthesia machine. For example, an absorption rate of oxygen into the blood of the patient via the oxygenator may be determined by the anesthesia machine (e.g., calculated by the electronic controller of the anesthesia machine) according to the equation $VO2=Q*(FiO2-FeO2)$ described above. A threshold oxygen absorption rate may correspond to a rate of oxygen absorption by the blood of the patient during conditions in which the patient is in a hypermetabolic state (e.g., a condition in which the blood absorbs an increased amount of oxygen relative to non-hypermetabolic states). If the absorption rate of oxygen determined by the anesthesia machine (e.g., VO2 in the equation above) is greater than the threshold oxygen absorption rate, the electronic controller of the anesthesia machine may determine that a leak or other degradation of the oxygenator, CPB machine, and/or anesthesia machine has occurred. In response to the determined leak or other degradation, the electronic controller may alert an operator of the anesthesia machine (e.g., an anesthesiologist) of the detected leak or degradation via one or more audible and/or visual indicators (e.g., audible alarms, images displayed on a graphical display device of the anesthesia machine, etc.)

In an example operation of the anesthesia system, the operator of the anesthesia machine may set a desired concentration of oxygen flowing from the anesthesia machine to the inlet of the oxygenator of the CPB machine via one or more user input devices of the anesthesia machine. The operator may additionally set a total flow rate of mixed gases from the anesthesia machine to the inlet of the oxygenator of the CPB machine. The anesthesia machine may measure the concentration of oxygen in exhaust gases flowing from the outlet of the oxygenator via the respiratory gas module of the anesthesia machine, and the electronic controller of the anesthesia machine may compare the concentration of oxygen at the outlet to the concentration of oxygen in the mixed gases flowing to the inlet. The electronic controller may calculate the oxygen absorption rate of the blood of the patient based on the oxygen concentration at the inlet and outlet of the oxygenator and the total flow rate of mixed gases to the inlet (e.g., via the equation $VO2=Q*(FiO2-FeO2)$ described above). The electronic controller may compare the calculated oxygen absorption rate to the threshold oxygen absorption rate, with the threshold oxygen absorption rate being a pre-determined oxygen absorption rate of the blood of the patient during conditions in which the patient is in a hypermetabolic state. If the calculated oxygen absorption rate exceeds the threshold oxygen absorption rate, the anesthesia machine may indicate to the operator that a gas leak and/or degradation of the anesthesia system has occurred.

In this way, the electronic controller of the anesthesia machine may be configured to determine gas exchange parameters of the oxygenator of the heart-lung machine based on one or more of oxygen concentration upstream and/or downstream of the oxygenator, carbon dioxide concentration upstream and/or downstream of the oxygenator, vaporized anesthetic agent concentration upstream and/or downstream of the oxygenator, arterial blood temperature, and mixed gas flow rate (e.g., the flow rate of the fresh gas/oxygen/vaporized anesthetic agent mix) through the oxygenator. In one example, if a gas exchange parameter does not meet a condition relative to a threshold, an operator may be notified. The gas exchange parameter may include an oxygen uptake rate at the oxygenator and if the oxygen uptake rate exceeds a threshold oxygen uptake rate, an operator may be notified that a leak in the system may be present. In another example, the gas exchange parameter may include a carbon dioxide expulsion rate of the oxygenator (e.g., indicative of the rate of carbon dioxide that is expelled from the patient's blood) and if the carbon dioxide expulsion rate is below a threshold, an operator may be notified that the carbon dioxide regulation (e.g. scavenging/removal) function of the system is degraded. For example, an arterial blood carbon dioxide tension may be determined based on a CO2 level exiting the oxygenator as measured by the anesthesia machine and a temperature of blood of a patient as measured by the arterial blood temperature sensor of the cardiopulmonary bypass machine. In one example, blood may flow into the oxygenator with a first amount (e.g., concentration) of dissolved CO2, and a portion of the dissolved CO2 is released as gaseous CO2 from the blood as the blood flows through the oxygenator. The amount of dissolved CO2 released from the blood as gaseous CO2 may increase as a temperature of the blood increases. At higher blood temperatures (e.g., 90 degrees Fahrenheit), CO2 may be released from the blood at an increased rate relative to lower blood temperatures (e.g., 85 degrees Fahrenheit). The temperature of the blood may be sent from a controller of the cardiopulmonary bypass machine to the anesthesia machine. If the arterial blood carbon dioxide tension is outside a threshold range of values (e.g., outside of 35-45 mmHg), an operator may be notified so that gas exchange parameters may be adjusted.

Figure 5:
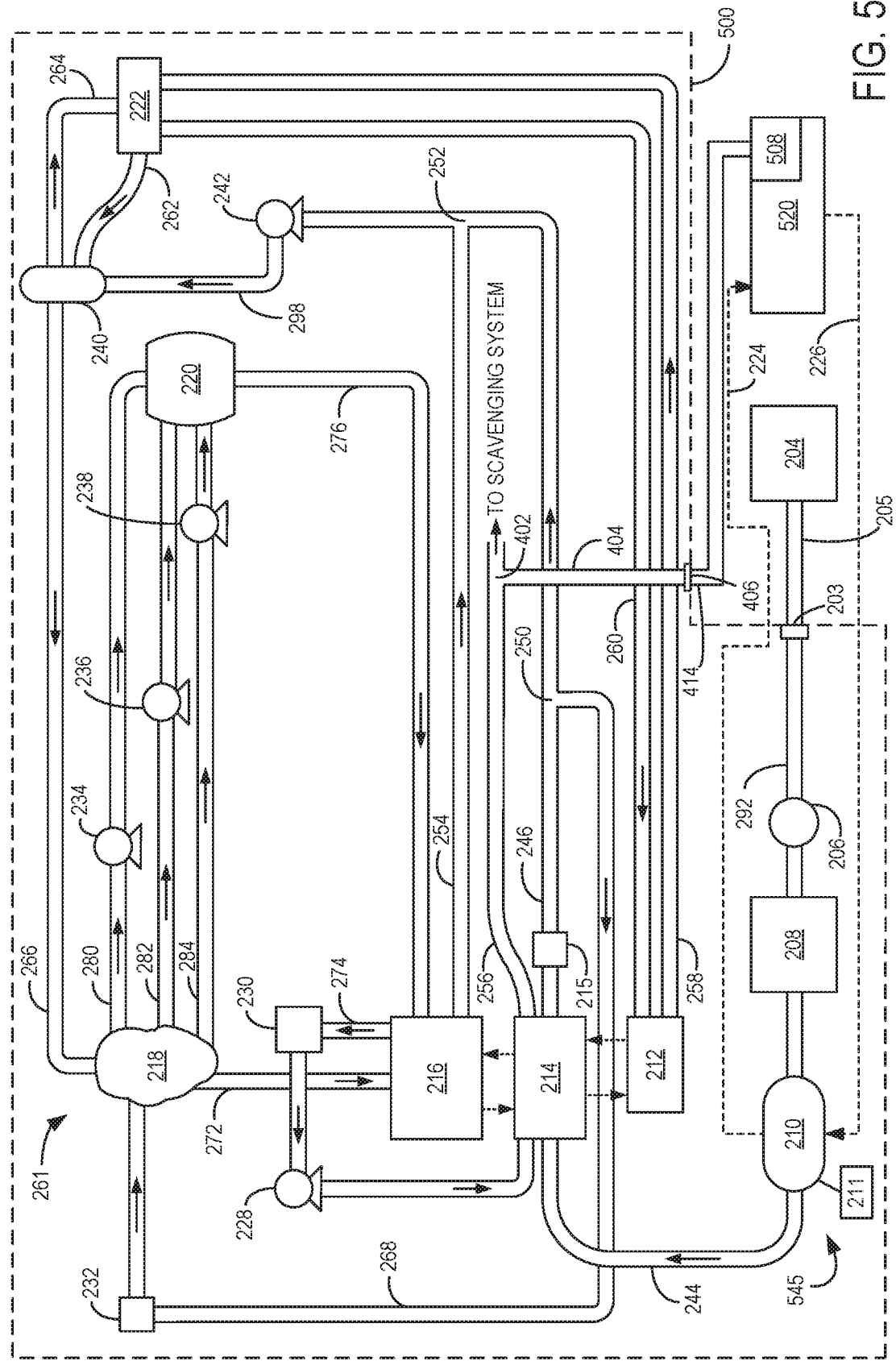
FIG. 5 schematically shows an anesthesia system including a vaporizer of a CPB machine in wireless communication with an anesthesia machine, and an outlet of an oxygenator of the CPB machine directly coupled to a respiratory gas module of the anesthesia machine, according to an embodiment of the invention.

FIG. 5 shows an anesthesia system 545 for a heart-lung machine 500 including various components similar to the components described above with reference to the heart-lung machine 200 shown by FIG. 2, the heart-lung machine 300 shown by FIG. 3, and the heart-lung machine 400 shown by FIG. 4. For example, heart-lung machine 500 includes venous reservoir 216, oxygenator 214, heat exchanger 212, cardiotomy reservoir 220, etc. In the example shown by FIG. 5, the oxygenator 214 receives fresh gases (e.g., oxygen, air, etc.) and vaporized anesthetic agents via the vaporizer 210 of the heart-lung machine 500, similar to the example described above with reference to FIG. 2. Additionally, the heart-lung machine 500 includes passage 404 coupled to second gas outlet 406 and passage 414 in order to provide a mixture of gases and vaporized anesthetic agents to a respiratory gas module 508 of anesthesia machine 520 (e.g., similar to the respiratory gas module 408 of the anesthesia machine 420 described above with reference to FIG. 4).

An electronic controller of the anesthesia machine 520 (e.g., similar to the electronic controllers of the anesthesia machines described above with reference to FIGS. 1-4) is configured to communicate electronically with the vaporizer 210 of the heart-lung machine 500, similar to the example described above with reference to FIG. 2. For example, a transmitter of the electronic controller of the anesthesia machine 520 may transmit wireless signals 226 to the electronic receiver of the vaporizer 210, and the transmitter of the vaporizer 210 may transmit wireless signals 224 to an electronic receiver of the anesthesia machine 520. In one example, the vaporizer 210 may transmit wireless signals including information about various operating parameters of the vaporizer 210 (as described above with reference to FIG. 2) to the electronic controller of the anesthesia machine 520, and the anesthesia machine 520 may store the information about the operating parameters into non-transitory memory and/or display the operating parameters to the operator of the anesthesia machine 520 via a graphical display device (e.g., display device 15 shown by FIG. 1A). In another example, the operator may set a desired vaporized anesthetic agent concentration via a user input device (e.g., keyboard, touchscreen, etc.) of the anesthesia machine 520, and in response, the electronic controller of the anesthesia machine 520 may transmit a wireless signal to the receiver of the vaporizer 210. The electronic controller of the vaporizer 210 may then adjust the concentration of vaporized anesthetic agent flowing from the vaporizer 210 to the oxygenator 214 by transmitting electrical signals to actuators of one or more valves of the vaporizer 210 in order to adjust the positions of the one or more valves (e.g., increase and/or decrease an amount of opening of the one or more valves).

In another example, the operator may input a desired absorption rate/arterial tension of anesthetic agents (e.g., absorption by the blood of the patient) at the anesthesia machine 520. The respiratory gas module 508 of the anesthesia machine 520 may measure a concentration of anesthetic agents flowing from the oxygenator 214, and may compare the measured concentration to a concentration of anesthetic agents flowing from the vaporizer 210 to the oxygenator 214. The anesthesia machine 520 receives information about the concentration of anesthetic agents flowing from the vaporizer 210 via wireless signals 224 transmitted by the vaporizer 210 to the anesthesia machine 520. The electronic controller of the anesthesia machine 520 may continuously measure the concentration of anesthetic agents flowing from the oxygenator 214 and may continuously compare the measured concentration to the concentration of anesthetic agents flowing from the vaporizer 210 (e.g., as determined from the wireless signals transmitted to the anesthesia machine 520 from the vaporizer 210). The anesthesia machine 520 transmits wireless signals to the vaporizer 210 in order to adjust operation of the vaporizer 210 (e.g., responsive to the measured concentration of anesthetic agents flowing from the vaporizer 210 and the measured concentration of anesthetic agents flowing from the oxygenator 214) to provide the desired absorption rate of anesthetic agents. For example, during conditions in which the electronic controller of the anesthesia machine 520 determines that a calculated absorption rate/blood tension is less than the desired absorption rate/blood tension (e.g., calculated by the electronic controller of the anesthesia machine 520 based on a difference between the concentration of anesthetic agents flowing into the oxygenator 214 and a concentration of anesthetic agents flowing out of the oxygenator 214, as described above), the electronic controller of the anesthesia machine 520 may transmit wireless signals to the vaporizer 210 to increase a flow rate of vaporized anesthetic agents from the vaporizer 210 to the oxygenator 214. The electronic controller of the vaporizer 210 transmits signals to actuators of one or more valves of the vaporizer 210 in response to the signals from the anesthesia machine 520 to increase the flow rate (e.g., by increasing an amount of opening of the one or more valves).

By configuring the anesthesia machine 520 and heart-lung machine 500 as described above, the anesthesia system may be utilized to provide closed loop control of volatile anesthetic agent delivered into the patient's blood stream via the oxygenator of the heart-lung machine by monitoring the anesthetic agent concentration into and out of the oxygenator. The anesthetic agent concentration input into the oxygenator may be delivered by the vaporizer of the heart-lung machine, and the vaporizer may transmit information about the concentration of anesthetic agent input into the oxygenator to the anesthesia machine. The output exhaust anesthetic agent concentration of the oxygenator may be monitored by the respiratory gas module of the anesthesia system. The difference between input and exhaust may be correlated/modeled to predict the tension of the anesthetic agent in the patient's arterial blood, thereby increasing an accuracy with which anesthetic agent may be dosed to the patient. Additionally, the vaporizer of the heart-lung machine may be remotely controlled by the anesthesia machine, increasing mobility in the operating room.

Figure 6A:
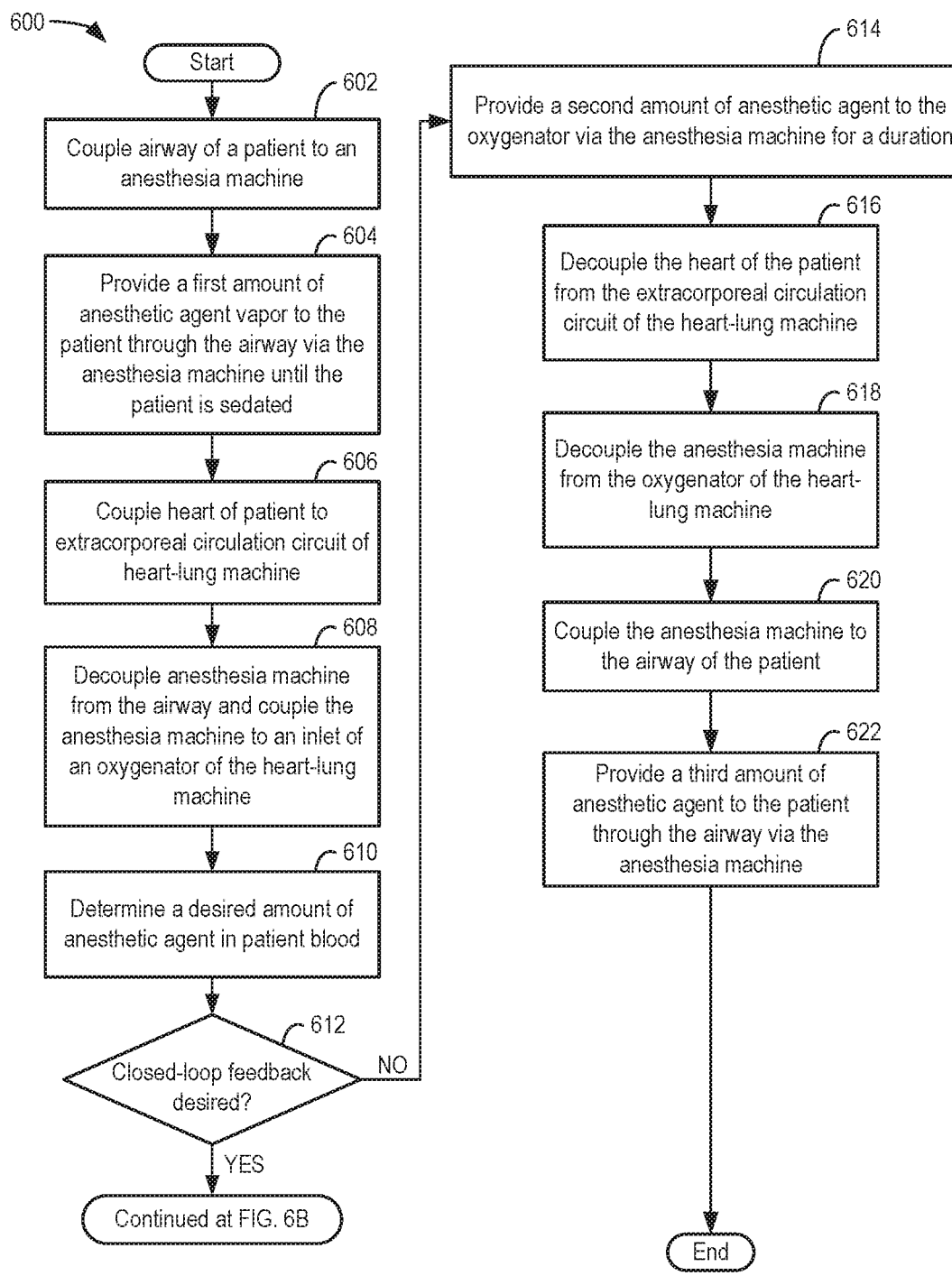
FIGS. 6A-6B illustrate a method of coupling an anesthesia machine to an airway of a patient to deliver vaporized anesthetic agent to the airway for a first duration, coupling the anesthesia machine to a CPB machine to adjust a concentration of anesthetic agent in the blood of the patient for a second duration, and resuming delivery of vaporized anesthetic agent to the airway for a third duration, according to an embodiment of the invention.
Figure 6B:
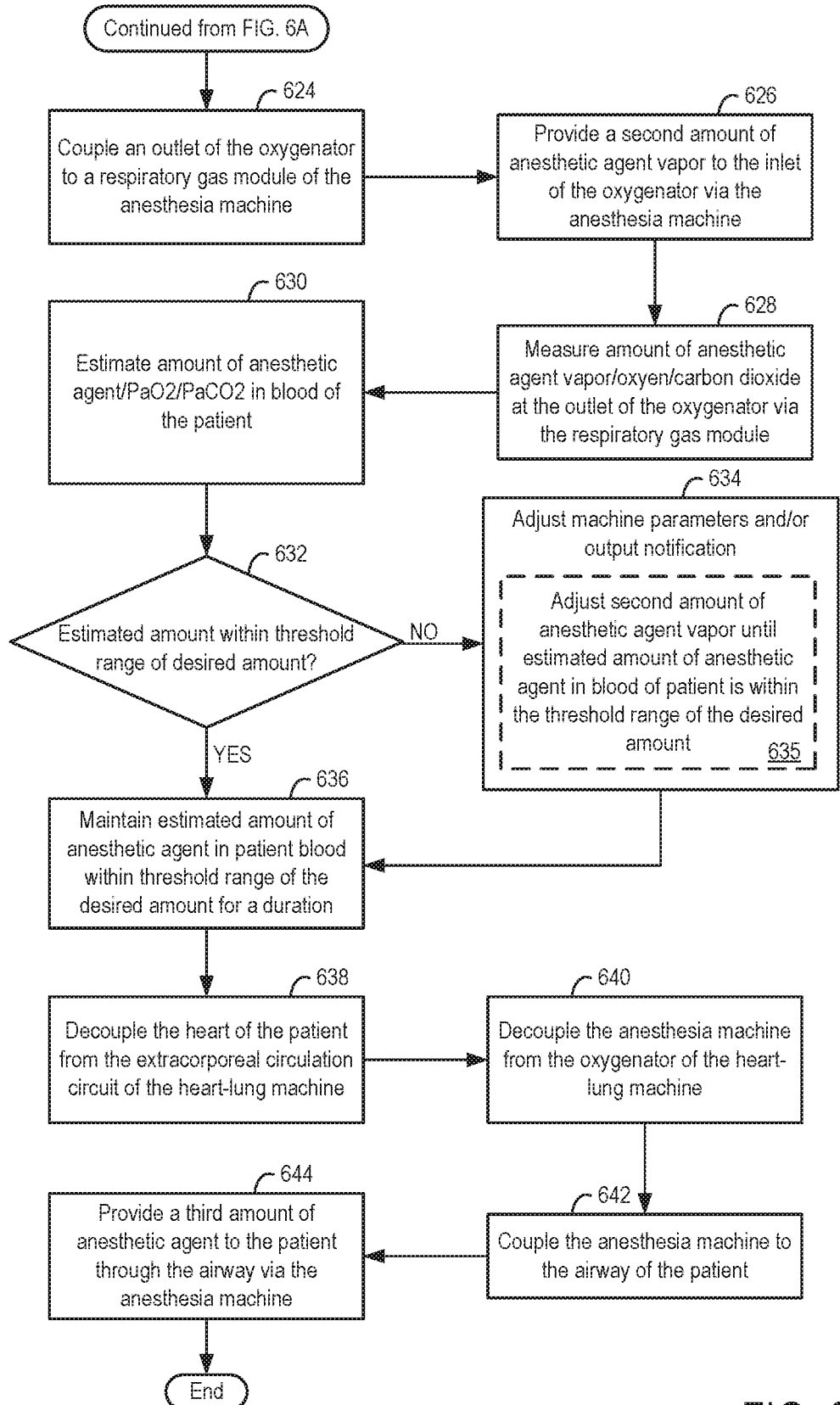

FIGS. 6A-6B show a method 600 for operating an anesthesia system having an anesthesia machine operably coupled to a heart-lung machine. Instructions for carrying out method 600 and the rest of the methods included herein may be executed by a controller based on instructions stored on a memory of the controller and in conjunction with signals received from sensors of the anesthesia system, such as the sensors described above with reference to FIGS. 1A-1C. The controller may employ actuators of anesthesia system to adjust operation of the components of the anesthesia system, according to the methods described below.

At 602, the method includes coupling an airway of a patient to the anesthesia machine. For example, the anesthesia machine (similar to the anesthesia machines 100, 202, 320, 420, and/or 520 described above) may include a breathing circuit adapted to couple to an airway (intubation tube, mouth, and/or nose) of the patient to provide the airway of the patient with gases from the anesthesia machine.

The method continues from 602 to 604 where the method includes providing a first amount of anesthetic agent vapor to the patient through the airway via the anesthesia machine until the patient is sedated. For example, a vaporizer of the anesthesia machine (e.g., similar to vaporizer 14 described above with reference to FIGS. 1A-1C) may vaporize liquid anesthetic agent stored in one or more containers on the anesthesia machine. The vaporizer may mix the vaporized anesthetic agent with gases (e.g., oxygen, air, etc.) and flow the mixture through the breathing circuit to the airway of the patient until the patient is sufficiently sedated for a cardiopulmonary bypass procedure (e.g., unconscious). The amount (e.g., concentration) of the anesthetic agent supplied to the breathing circuit may be controlled (e.g., manually by an anesthesiologist or automatically by the controller of the anesthesia machine) based on output from the respiratory gas module. For example, the respiratory gas module may measure the end-tidal concentration of the anesthetic agent mixed with the gases in the breathing circuit and allow for control of the concentration of anesthetic agent relative to the minimum alveolar concentration, adjusted for patient age, ambient temperature, and ambient pressure, for example.

The method continues from 604 to 606 where the method includes coupling the heart of patient to an extracorporeal circulation circuit of the heart-lung machine. For example, one or more passages of the heart-lung machine may be coupled to the heart in order to flow blood to and/or from the heart (e.g., passages 280, 282, 284, 272, 266, and 268 described above).

The method continues from 606 to 608 where the method includes decoupling the anesthesia machine from the airway and coupling the anesthesia machine to an inlet of an oxygenator of the heart-lung machine. During the cardiopulmonary bypass procedure, the lungs of the patient are often deflated to enable access to the heart of the patient. Because the lungs of the patient do not perform respiratory functions during the procedure, the anesthesia machine is coupled to the inlet of the oxygenator to deliver anesthetic agents and gases (e.g., oxygen) directly to the blood of the patient via the oxygenator.

The method continues 608 to 610 where the method includes determining a desired amount of anesthetic agent in the blood of the patient. For example, an operator of the anesthesia system (e.g., an anesthesiologist) may determine a desired concentration of anesthetic agent to be provided to the patient based on a height, weight, volume of blood, or other characteristics of the patient.

The method continues from 610 to 612 where the method includes determining whether closed-loop feedback is desired. For example, the operator may determine that closed-loop feedback is desired during conditions in which automatic adjustment of anesthetic agent from the anesthesia machine to the oxygenator is desired (e.g., automatic adjustment of the amount of anesthetic agent flowing from the anesthesia machine by an electronic controller of the anesthesia machine, without manual adjustment by the operator).

If closed-loop feedback is desired, the method continues from 612 to 624 (shown by FIG. 6B) where the method includes coupling an outlet of the oxygenator to a respiratory gas module of the anesthesia machine. For example, the passage 256 shown by FIG. 4 may be fluidly coupled to the respiratory gas module 408 of the anesthesia machine 420 shown by FIG. 4 in order to flow gases from the oxygenator to the anesthesia machine.

The method continues from 624 to 626 where the method includes providing a second amount of anesthetic agent vapor to the inlet of the oxygenator via the anesthesia machine. In one example, the second amount of anesthetic agent vapor may be based on an amount (e.g., a concentration) of anesthetic agent vapor to be supplied to the patient in order to maintain the patient in the sedated condition. In some examples, the second amount may be different than the first amount (e.g., more or less than the first amount).

The method continues from 626 to 628 where the method includes measuring an amount of anesthetic agent vapor, oxygen, and/or carbon dioxide at the outlet of the oxygenator via the respiratory gas module. For example, the respiratory gas module may measure a concentration of anesthetic agent vapor flowing out the oxygenator (e.g., via passage 256) as well as a concentration of oxygen and carbon dioxide.

The method continues from 628 to 630 where the method includes estimating an amount of anesthetic agent in the blood of the patient based on a difference between the second amount of anesthetic agent vapor and the measured amount of anesthetic agent vapor. The electronic controller of the anesthesia machine may include instructions stored in non-transitory memory for estimating the amount of anesthetic agent in the blood of the patient. For example, the controller may infer the amount of anesthetic agent absorbed by the blood (e.g., a rate of absorption) by comparing the concentration of vaporized anesthetic agent flowing out of the anesthesia machine to the oxygenator relative to the concentration of vaporized anesthetic agent in gases flowing to the respiratory gas module via the outlet of the oxygenator.

Additionally, arterial tensions of oxygen (PaO2) and carbon dioxide (PaCo2) in the blood of the patient may be determined based on the measured oxygen concentration and carbon dioxide concentration, respectively, and further based on arterial blood temperature. The electronic controller of the anesthesia machine may include instructions stored in non-transitory memory for estimating the PaO2 and PaCO2 in the blood of the patient. For example, the electronic controller of the anesthesia machine may include a look-up table that maps carbon dioxide concentration to PaCO2 as a function of arterial blood temperature. During certain arterial blood temperature conditions, such as when the blood is cooled or when the blood is at a stable hypothermic temperature, the carbon dioxide concentration may accurately correlate to PaCO2. However, as the blood temperature increases back to normal body temperature, the correlation may deviate. Thus, the look-up table may include carbon dioxide concentration and arterial blood temperature as inputs and may output PaCO2. A similar look-up table for PaO2 may also be stored in memory of the electronic controller of the anesthesia machine.

The method continues from 630 to 632 where the method includes determining whether the estimated amounts of vaporized agent, PaO2, and/or PaCO2 are within respective threshold ranges of desired amounts. The desired amount of vaporized agent may be based on the user input, as described above. The desired PaO2 and PaCO2 may be predetermined physiological levels taking into account current ambient pressure, for example. In one example, the threshold range of vaporized anesthetic agent amount and/or threshold ranges of PaO2 and PaCO2 may be pre-determined threshold ranges (e.g., within a percentage of the desired amount) stored in non-transitory memory of the controller (e.g., in a lookup table of the controller). In other examples, the threshold ranges may be input into an input device (e.g., keyboard, touchscreen, etc.) of the anesthesia machine by the operator of the anesthesia system.

If the estimated amounts of vaporized agent, PaO2, and/or PaCO2 are not within the respective threshold ranges of the respective desired amounts at 632, the method continues from 632 to 634 where the method includes adjusting anesthesia machine and/or heart-lung machine parameters and/or outputting a notification. For example, as indicated at 635, adjusting anesthesia machine parameters may include adjusting the second amount of anesthetic agent vapor until the estimated amount of anesthetic agent in the blood of patient is within the threshold range of the desired amount. In other examples, a notification (e.g., in the form of a display device element) may be output indicative of the PaO2 and/or PaCO2. In still further examples, the flow rate of oxygen at the anesthesia machine may be adjusted based on the PaO2, and so forth. The method then continues from 634 to 636, described below. For example, if the estimated amount of vaporized anesthetic agent exceeds an amount corresponding to an upper value of the threshold range, the electronic controller of the anesthesia machine may decrease the concentration of anesthetic agent flowing from the anesthesia machine and continuously estimate the amount of anesthetic agent in the blood of the patient until the estimated amount is within the threshold range.

However, if the estimated amount is within the threshold range of the desired amount at 632, the method continues from 632 to 636 where the method includes maintaining the estimated amount of anesthetic agent in the blood of the patient within the threshold range of the desired amount for a duration. In one example, the estimated amount may be maintained within the threshold range for a duration of the cardiopulmonary bypass procedure (e.g., the duration in which the blood of the patient circulates through the heart-lung machine).

The method continues from 636 to 638 where the method includes decoupling the heart of the patient from the extracorporeal circulation circuit of the heart-lung machine. For example, the heart-lung machine may be decoupled from the patient so that the patient resumes normal heart and respiratory functions (e.g., the heart of the patient pumps blood through the body of the patient, rather than the heart-lung machine pumping blood through the patient).

The method continues from 638 to 640 where the method includes decoupling the anesthesia machine from the oxygenator of the heart-lung machine. Because the extracorporeal circulation circuit of the heart-lung machine is not coupled to the heart of the patient, oxygenation of the blood of the patient is performed via respiration and not via the oxygenator. Sedation of the patient via vaporized anesthetic agents delivered to the oxygenator from the anesthesia machine is stopped.

The method continues from 640 to 642 where the method includes coupling the anesthesia machine to the airway of the patient. For example, the breathing circuit of the anesthesia machine may be recoupled to the airway (endotracheal tube) of the patient in order to resume sedation of the patient via respiration of vaporized anesthetic agents, as described below.

The method continues from 642 to 644 where the method includes providing a third amount of anesthetic agent to the patient through the airway via the anesthesia machine. In some examples, the third amount may be a same amount as the first amount. In other examples, the third amount may be a different amount based on the previously estimated concentration of anesthetic agents within the blood of the patient (e.g., the concentration due to absorption of the anesthetic agents via the oxygenator as described above).

If closed-loop feedback is not desired at 612, the method continues from 612 to 614 (shown by FIG. 6A) where the method includes providing a second amount of anesthetic agent to the oxygenator via the anesthesia machine for a duration. In one example, the second amount of anesthetic agent vapor may be based on an amount (e.g., a concentration) of anesthetic agent vapor to be supplied to the patient in order to maintain the patient in the sedated condition. In some examples, the second amount may be different than the first amount (e.g., more or less than the first amount). The second amount may be based on a height, a weight, and/or other characteristics of the patient and may be pre-determined by the operator of the anesthesia machine. In some examples, the operator may adjust the second amount in response to an amount of sedation of the patient and/or a volume of blood flowing through the heart-lung machine.

The method continues from 614 to 616 where the method includes decoupling the heart of the patient from the extracorporeal circulation circuit of the heart-lung machine. For example, the heart-lung machine may be decoupled from the patient so that the patient resumes normal heart and respiratory functions (e.g., the heart of the patient pumps blood through the body of the patient, rather than the heart-lung machine pumping blood through the patient).

The method continues from 616 to 618 where the method includes decoupling the anesthesia machine from the oxygenator of the heart-lung machine. During the cardiopulmonary bypass procedure, the lungs of the patient are often deflated to enable access to the heart of the patient. Because the lungs of the patient do not perform respiratory functions during the procedure, the anesthesia machine is coupled to the inlet of the oxygenator to deliver anesthetic agents and gases (e.g., oxygen) directly to the blood of the patient via the oxygenator.

The method continues from 618 to 620 where the method includes coupling the anesthesia machine to the airway of the patient. For example, the breathing circuit of the anesthesia machine may be recoupled to the airway (endotracheal tube) of the patient in order to resume sedation of the patient via respiration of vaporized anesthetic agents, as described below.

The method continues from 620 to 622 where the method includes providing a third amount of anesthetic agent to the patient through the airway via the anesthesia machine. In some examples, the third amount may be a same amount as the first amount or second amount. In other examples, the third amount may be a different amount based on the estimated concentration of anesthetic agents within the blood of the patient (e.g., the concentration due to absorption of the anesthetic agents via the oxygenator as described above).

Thus, the systems and methods described herein provide for improved clinician/team workflow, reduced risk of light anesthesia with awareness and recall, and facilitation of automated anesthesia electronic record-keeping during cardiac bypass. The embodiments disclosed herein enables continuity of the patient's anesthetic management plan during CPB by allowing the anesthesiologist and perfusionist a convenient/seamless transition in communicating anesthesia parameters (e.g., mixed gas settings, target anesthetic concentration, oxygen and carbon dioxide exchange, etc.) between conventional inhalational anesthesia (mechanical ventilation of patient) and CPB (membrane oxygenator) maintenance anesthesia.

A technical effect of the disclosure is to enable the anesthesia machine to receive information related to anesthetic agent parameters during CPB, such as concentrations provided to the oxygenator of the heart-lung machine via the vaporizer. The vaporizer transmits signals (e.g., wireless signals) to the anesthesia machine, and the anesthesia machine stores the information in memory, displays the information, and/or sends the information to coupled devices. Another technical effect of the disclosure is automated control of the concentration of anesthetic agent provided to a patient during CPB.

In one embodiment, a system comprises: a cardiopulmonary bypass machine; and an anesthesia machine configured to operably couple to the cardiopulmonary bypass machine, the anesthesia machine adapted to control a flow of vapor through the cardiopulmonary bypass machine. In a first example of the system, an electronic controller of the anesthesia machine is configured to wirelessly couple to a transmitter of the cardiopulmonary bypass machine, the electronic controller being adapted to receive cardiopulmonary bypass machine operating parameter information from the transmitter. A second example of the system optionally includes the first example, and further includes a graphical display device of the anesthesia machine electrically coupled to the electronic controller, the graphical display device being adapted to display the cardiopulmonary bypass machine operating parameter information. A third example of the system optionally includes one or both of the first and second examples, and further includes wherein an outlet of an oxygenator of the cardiopulmonary bypass machine is configured to directly couple to an inlet of the anesthesia machine. A fourth example of the system optionally includes one or more or each of the first through third examples, and further includes wherein the inlet of the anesthesia machine is a respiratory gas module of the anesthesia machine including a plurality of sensors adapted to measure an amount of vaporized anesthetic agent in the flow of vapor through the cardiopulmonary bypass machine. A fifth example of the system optionally includes one or more or each of the first through fourth examples, and further includes wherein the electronic controller includes instructions stored in non-transitory memory for adjusting the flow of vapor through the cardiopulmonary bypass machine responsive to the measured amount of vaporized anesthetic agent. A sixth example of the system optionally includes one or more or each of the first through fifth examples, and further includes wherein an outlet of the anesthesia machine is configured to directly couple to an inlet of an oxygenator of the cardiopulmonary bypass machine. A seventh example of the system optionally includes one or more or each of the first through sixth examples, and further includes wherein an outlet of the oxygenator of the cardiopulmonary bypass machine is configured to directly coupled to a respiratory gas module of the anesthesia machine.

In another embodiment, a system comprises: a cardiopulmonary bypass machine including a vaporizer, the vaporizer having a plurality of sensors and an electronic transmitter; and an anesthesia machine including an electronic controller adapted to receive wireless signals transmitted by the transmitter. In a first example of the system, a gas outlet of an oxygenator of the cardiopulmonary bypass machine is configured to directly couple to a gas inlet of the anesthesia machine. A second example of the system optionally includes the first example, and further includes wherein a gas inlet of the anesthesia machine includes a plurality of sensors adapted to measure a concentration of vaporized anesthetic agents in gases flowing from the oxygenator to the gas inlet, the plurality of sensors being in electronic communication with the electronic controller of the anesthesia machine. A third example of the system optionally includes one or both of the first and second examples, and further includes wherein the plurality of sensors are adapted to measure a concentration of vaporized anesthetic agents in gases flowing from the vaporizer to the oxygenator, and wherein the electronic transmitter of the vaporizer transmits the measured concentration to the electronic controller of the anesthesia machine. A fourth example of the system optionally includes one or more or each of the first through third examples, and further includes wherein the electronic controller of the anesthesia machine includes instructions stored in non-transitory memory for determining a rate of absorption of anesthetic agent into blood flowing through the cardiopulmonary bypass machine responsive to the measured concentration transmitted by the vaporizer and the measured concentration in gases flowing from the oxygenator to the gas inlet. A fifth example of the system optionally includes one or more or each of the first through fourth examples, and further includes wherein the electronic transmitter of the vaporizer is electrically coupled to an electronic controller of the vaporizer, the electronic controller being electrically coupled to the plurality of sensors and adapted to receive electrical signals from the plurality of sensors. A sixth example of the system optionally includes one or more or each of the first through fifth examples, and further includes wherein the electronic controller of the vaporizer includes instructions stored in non-transitory memory for adjusting a concentration of vaporized anesthetic agent at an outlet of the vaporizer responsive to signals transmitted to the electronic controller of the vaporizer by an electronic transmitter of the anesthesia machine.

In one embodiment, a method for operating an anesthesia machine comprises: flowing vaporized anesthetic agent from the anesthesia machine to an airway of a patient via an anesthesia breathing circuit; and measuring an amount of vaporized anesthetic agent flowing from an outlet of an oxygenator of a cardiopulmonary bypass machine with the anesthesia machine. In a first example of the method, the method further comprises flowing vaporized anesthetic agent from the anesthesia machine to the oxygenator of the cardiopulmonary bypass machine, and adjusting the flow of vaporized anesthetic agent from the anesthesia machine to the oxygenator of the cardiopulmonary bypass machine responsive to the measured amount of vaporized anesthetic agent flowing from the outlet of the oxygenator. A second example of the method optionally includes the first example, and further includes determining, with the anesthesia machine, a gas exchange parameter of the oxygenator and outputting a notification to an operator if the gas exchange parameter does not meet a condition relative to a threshold. A third example of the method optionally includes one or both of the first and second examples, and further includes wirelessly receiving cardiopulmonary bypass machine operating parameter information at an electronic controller of the anesthesia machine from a transmitter of the cardiopulmonary bypass machine. A fourth example of the method optionally includes one or more or each of the first through third examples, and further includes wherein flowing vaporized anesthetic agent from the anesthesia machine to the airway of a patient occurs prior to flowing vaporized anesthetic agent from the anesthesia machine to the oxygenator of the cardiopulmonary bypass machine during a single cardiopulmonary bypass procedure.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A system, comprising:
a cardiopulmonary bypass machine including a vaporizer, the vaporizer having a first plurality of sensors and an electronic transmitter; and
an anesthesia machine configured to operably couple to the cardiopulmonary bypass machine, the anesthesia machine adapted to control a flow of vapor through the cardiopulmonary bypass machine;
wherein an electronic controller of the anesthesia machine is configured to wirelessly couple to the electronic transmitter of the vaporizer of the cardiopulmonary bypass machine.

2. The system of claim 1, wherein the electronic controller of the anesthesia machine is adapted to receive vaporizer operating parameter information sensed by the first plurality of sensors from the electronic transmitter.

3. The system of claim 2, further comprising a graphical display device of the anesthesia machine electrically coupled to the electronic controller, the graphical display device being adapted to display the vaporizer operating parameter information.

4. The system of claim 2, wherein an outlet of an oxygenator of the cardiopulmonary bypass machine is configured to directly couple to an inlet of the anesthesia machine.

5. The system of claim 4, wherein the inlet of the anesthesia machine is a respiratory gas module of the anesthesia machine including a second plurality of sensors adapted to measure an amount of vaporized anesthetic agent in the flow of vapor through the cardiopulmonary bypass machine.

6. The system of claim 5, wherein the electronic controller includes instructions stored in non-transitory memory for adjusting the flow of vapor through the cardiopulmonary bypass machine responsive to the measured amount of vaporized anesthetic agent.

7. The system of claim 1, wherein an outlet of the anesthesia machine is configured to directly couple to an inlet of an oxygenator of the cardiopulmonary bypass machine.

8. The system of claim 7, wherein an outlet of the oxygenator of the cardiopulmonary bypass machine is configured to directly coupled to a respiratory gas module of the anesthesia machine.

9. A system, comprising:
a cardiopulmonary bypass machine including a vaporizer, the vaporizer having a first plurality of sensors and an electronic transmitter; and
an anesthesia machine including an electronic controller adapted to receive wireless signals transmitted by the electronic transmitter.

10. The system of claim 9, wherein a gas outlet of an oxygenator of the cardiopulmonary bypass machine is configured to directly couple to a gas inlet of the anesthesia machine.

11. The system of claim 10, wherein the gas inlet of the anesthesia machine includes a second plurality of sensors adapted to measure a first concentration of vaporized anesthetic agents in gases flowing from the oxygenator to the gas inlet, the second plurality of sensors being in electronic communication with the electronic controller of the anesthesia machine.

12. The system of claim 11, wherein the first plurality of sensors is adapted to measure a second concentration of vaporized anesthetic agents in gases flowing from the vaporizer to the oxygenator, and wherein the electronic transmitter of the vaporizer transmits the second concentration to the electronic controller of the anesthesia machine.

13. The system of claim 12, wherein the electronic controller of the anesthesia machine includes instructions stored in non-transitory memory for determining a rate of absorption of anesthetic agent into blood flowing through the cardiopulmonary bypass machine responsive to the second concentration transmitted by the vaporizer and the first concentration in gases flowing from the oxygenator to the gas inlet.

14. The system of claim 9, wherein the electronic transmitter of the vaporizer is electrically coupled to a second electronic controller of the vaporizer, the second electronic controller being electrically coupled to the first plurality of sensors and adapted to receive electrical signals from the first plurality of sensors.

15. The system of claim 14, wherein the second electronic controller of the vaporizer includes instructions stored in non-transitory memory for adjusting a concentration of vaporized anesthetic agent at an outlet of the vaporizer responsive to signals transmitted to the second electronic controller of the vaporizer by a second electronic transmitter of the anesthesia machine.

16. A method for operating an anesthesia machine, comprising:
flowing vaporized anesthetic agent from the anesthesia machine to an airway of a patient via an anesthesia breathing circuit; and
measuring an amount of vaporized anesthetic agent flowing from an outlet of an oxygenator of a cardiopulmonary bypass machine with the anesthesia machine.

17. The method of claim 16, further comprising flowing the vaporized anesthetic agent from the anesthesia machine to the oxygenator of the cardiopulmonary bypass machine, and adjusting a flow of vaporized anesthetic agent from the anesthesia machine to the oxygenator of the cardiopulmonary bypass machine responsive to the measured amount of vaporized anesthetic agent flowing from the outlet of the oxygenator.

18. The method of claim 17, further comprising determining, with the anesthesia machine, a gas exchange parameter of the oxygenator and outputting a notification to an operator if the gas exchange parameter does not meet a condition relative to a threshold.

19. The method of claim 17, further comprising wirelessly receiving cardiopulmonary bypass machine operating parameter information at an electronic controller of the anesthesia machine from a transmitter of the cardiopulmonary bypass machine.

20. The method of claim 17, wherein flowing the vaporized anesthetic agent from the anesthesia machine to the airway of the patient occurs prior to flowing the vaporized anesthetic agent from the anesthesia machine to the oxygenator of the cardiopulmonary bypass machine during a single cardiopulmonary bypass procedure.

* * * * *